United States Patent
Vandike et al.

(10) Patent No.: US 12,178,157 B2
(45) Date of Patent: *Dec. 31, 2024

(54) CROP STATE MAP GENERATION AND CONTROL SYSTEM

(71) Applicant: Deere & Company, Moline, IL (US)

(72) Inventors: Nathan R. Vandike, Geneseo, IL (US); Bhanu Kiran Reddy Palla, Bettendorf, IA (US); Noel W. Anderson, Fargo, ND (US); Federico Pardina-Malbran, Fort Collins, CO (US)

(73) Assignee: Deere & Company, Moline, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,230

(22) Filed: Aug. 8, 2023

(65) Prior Publication Data

US 2023/0397532 A1   Dec. 14, 2023

Related U.S. Application Data

(63) Continuation of application No. 17/067,025, filed on Oct. 9, 2020, now Pat. No. 11,849,671.

(51) Int. Cl.
| | |
|---|---|
| *A01B 79/00* | (2006.01) |
| *A01D 41/127* | (2006.01) |
| *G01B 11/06* | (2006.01) |
| *G01N 33/00* | (2006.01) |
| *G01S 19/01* | (2010.01) |

(Continued)

(52) U.S. Cl.
CPC ........ *A01D 41/127* (2013.01); *G01B 11/0608* (2013.01); *G01N 33/0098* (2013.01); *G01S 19/01* (2013.01); *G06N 20/00* (2019.01); *A01D 41/1278* (2013.01); *A01D 41/141* (2013.01)

(58) Field of Classification Search
CPC ............................. A02B 79/005; A02B 79/00
See application file for complete search history.

(56) References Cited

U.S. PATENT DOCUMENTS

| | | |
|---|---|---|
| 5,995,895 A | 11/1999 | Watt et al. |
| 6,266,595 B1 | 7/2001 | Greatline et al. |
| 8,849,523 B1 | 9/2014 | Chan et al. |

(Continued)

OTHER PUBLICATIONS

Prosecution History in U.S. Appl. No. 17/067,025 including: Application and Drawings filed on Oct. 9, 2020, Non Final Office Action dated Mar. 28, 2023 and Notice of Allowance dated Sep. 7, 2023. 68 pages.

*Primary Examiner* — Tan Q Nguyen
(74) *Attorney, Agent, or Firm* — Kelly, Holt & Christenson; Joseph R. Kelly

(57) ABSTRACT

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control.

20 Claims, 11 Drawing Sheets

(51) Int. Cl.
*G06N 20/00* (2019.01)
*A01D 41/14* (2006.01)

(56) References Cited

U.S. PATENT DOCUMENTS

2005/0025387 A1* 2/2005 Luo .................... H04N 1/3875
382/173
2022/0110247 A1 4/2022 Vandike et al.
2023/0354795 A1* 11/2023 Aronov ................ A01N 63/14

* cited by examiner

CROP STATE MAP GENERATION AND CONTROL SYSTEM

CROSS-REFERENCE TO RELATED APPLICATION

The present application is a continuation of and claims priority of U.S. patent application Ser. No. 17/067,025, filed Oct. 9, 2020, the content of which is hereby incorporated by reference in its entirety.

FIELD OF THE DESCRIPTION

The present description relates to agricultural machines, forestry machines, construction machines and turf management machines.

BACKGROUND

There are a wide variety of different types of agricultural machines. Some agricultural machines include harvesters, such as combine harvesters, sugar cane harvesters, cotton harvesters, self-propelled forage harvesters, and windrowers. Some harvester can also be fitted with different types of headers to harvest different types of crops.

Agricultural harvesters may operate differently in areas of a field containing downed crop. Downed crop refers to crop plants that have their stalks bent or broken, for example due to wind, rain, hail, or the like. These forces bend or break the stalks the crop plants and cause the plants to have a bent-over and non-vertical orientation. Crop state is an agricultural characteristic indicative of whether a crop plant is standing, down, partially down, stubble, or missing and, if the crop is downed, the compass orientation and magnitude of the downing.

The discussion above is merely provided for general background information and is not intended to be used as an aid in determining the scope of the claimed subject matter.

SUMMARY

A prior vegetative index map, seeding characteristic map, predictive yield map, or predictive biomass map is obtained by an agricultural harvester and shows one of vegetative index, seeding characteristic, predictive yield, or predictive biomass values at different geographic locations of a field and may be particularly useful during harvesting of the field. An in-situ sensor on the agricultural harvester senses a characteristic that has values indicative of the crop state proximate the agricultural harvester as the agricultural harvester moves through the field. A predictive map generator generates a functional predictive map that predicts crop state at different locations in the field based on a relationship between the values in the vegetative index, seeding characteristic, predictive yield, or predictive biomass map and the crop state characteristic sensed by the in-situ sensor. The functional predictive crop state map can be output and used in automated machine control.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to examples that solve any or all disadvantages noted in the background.

DETAILED DESCRIPTION

Figure 1:
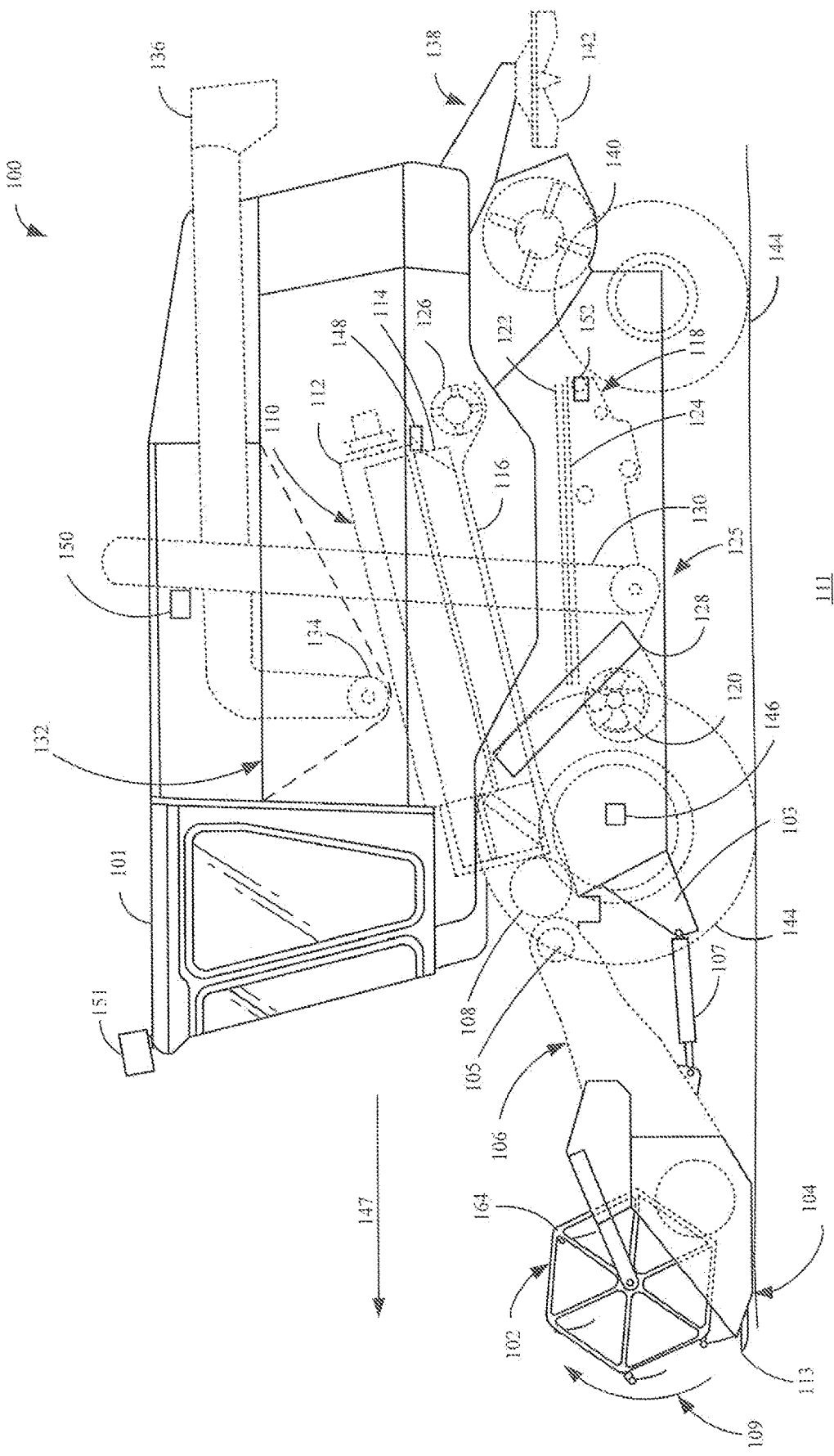
FIG. 1 is a partial pictorial, partial schematic illustration of one example of an agricultural harvester.

For the purposes of promoting an understanding of the principles of the present disclosure, reference will now be made to the examples illustrated in the drawings, and specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, and/or steps described with respect to one example may be combined with the features, components, and/or steps described with respect to other examples of the present disclosure.

The present description relates to using in-situ data taken concurrently with an agricultural operation, in combination with prior data, to generate a functional predictive map and, more particularly, a functional predictive crop state map. In some examples, the functional predictive crop state map can be used to control an agricultural work machine, such as an agricultural harvester. Performance of an agricultural harvester may be degraded when the agricultural harvester engages areas of varying crop state unless machine settings are also changed. For instance, in an area of downed crop the agricultural harvester may travel more slowly through the field to prevent grain loss. Or for instance, in an area of down crop, it may be beneficial to direct the agricultural harvester along a path such that the agricultural harvester harvests in a direction opposite the direction the crop is leaning of the down crop. That is, a course of the agricultural harvester is selected so as to drive the agricultural harvester into the crop plants from the opposite direction the plants are downed, such that the harvester reaches the top of the plant first. Or, for instance, in an area of down crop, it may be beneficial to adjust header height or reel positions.

A vegetative index map illustratively maps vegetative index values (which may be indicative of vegetative growth) across different geographic locations in a field of interest. One example of a vegetative index includes a normalized difference vegetation index (NDVI). There are many other vegetative indices, and these other vegetative indices are within the scope of the present disclosure. In some examples, a vegetative index may be derived from sensor readings of one or more bands of electromagnetic radiation reflected by plants. Without limitations, these bands may be in the microwave, infrared, visible, or ultraviolet portions of the electromagnetic spectrum.

A vegetative index map can thus be used to identify the presence and location of vegetation. In some examples, a vegetative index map enables crops to be identified and georeferenced in the presence of bare soil, crop residue, or other plants, including crop or weeds. For instance, towards the beginning of a growing season, when a crop is in a growing state, the vegetative index may show the progress of the crop development. Therefore, if a vegetative index map is generated early in the growing season or midway through the growing season, the vegetative index map may be indicative of the progress of the development of the crop plants. For instance, the vegetative index map may indicate whether the plant is stunted, whether a sufficient canopy is being established, or whether other plant attributes indicative of plant development are present. A vegetative index map can also be indicative of other vegetative characteristics as well such as plant health.

A seeding characteristic map illustratively maps seed locations across different geographic locations in one or more field of interest. These seed maps are typically collected from past seed planting operations. In some examples, the seeding characteristic map may be derived from control signals used by a seeder when planting the seeds or from sensor signals generated by sensors on the seeder that confirm a seed was planted. Seeders can include geographic position sensors that geolocate the locations of where the seeds were planted. This information can be used to determine the seed planting density which correlates to a plant density. Plant density can affect how resistant crop plants are to downing by wind, for example. A seeding characteristic map can also contain other information as well, such as characteristics of the seed used. For example, some characteristics include seed type, genetic stalk strength, genetic green snap susceptibility, seed brand, seed coating, planting date, gemination period, typical growth stage periods, mature plant height, and seed genotype The present discussion also includes predictive maps that predict a characteristic based on an information map and a relationship to sensed data obtained from an in-situ sensor. These predictive maps include a predictive yield map and a predictive biomass map. In one example, the predictive yield map is generated by receiving a prior vegetative index map and sensed yield data obtained from an in-situ yield sensor and determining a relationship between the prior vegetative index map and the sensed yield data obtained from a signal from the in-situ yield sensor, and using the relationship to generate the predictive yield map based on the relationship and the prior vegetative index map. In one example, the predictive biomass map is generated by receiving a prior vegetative index map and sensing a biomass and determining a relationship between the prior vegetative index map and the sensed biomass obtained from a data signal from a biomass sensor, and using the relationship to generate the predictive biomass map based on the relationship and the prior vegetative index map. The predictive yield and biomass maps can be created based on other information maps or generated in other ways as well. For example, the predictive yield or biomass maps can be generated based on satellite images, growth models, weather models, etc. Or for example, a predictive yield map or a predictive biomass map may be based in whole or in part on a topographic map, a soil type map, a soil constituent map, or a soil health map.

The present discussion thus proceeds with respect to examples in which a system receives one or more of a vegetative index, seeding, predictive yield, or predictive biomass map and uses an in-situ sensor that detects a variable indicative of crop state during a harvesting operation. The system generates a model that models a relationship between the vegetative index values, seed characteristic values, predictive yield values, or predictive biomass values from the one or more received maps and in-situ data from the in-situ sensor that represents the variable indicative of crop state. The model is used to generate a functional predictive crop state map that predicts an anticipated crop state in the field. The functional predictive crop state map, generated during the harvesting operation, can be presented to an operator or other user, used in automatically controlling an agricultural harvester during the harvesting operation, or both.

FIG. 1 is a partial pictorial, partial schematic, illustration of a self-propelled agricultural harvester 100. In the illustrated example, agricultural harvester 100 is a combine harvester. Further, although combine harvesters are provided as examples throughout the present disclosure, it will be appreciated that the present description is also applicable to other types of harvesters, such as cotton harvesters, sugarcane harvesters, self-propelled forage harvesters, windrowers, or other agricultural work machines. Consequently, the present disclosure is intended to encompass the various types of harvesters described and is, thus, not limited to combine harvesters. Moreover, the present disclosure is directed to other types of work machines, such as agricultural seeders and sprayers, construction equipment, forestry equipment, and turf management equipment where generation of a predictive map may be applicable. Consequently, the present disclosure is intended to encompass these various types of harvesters and other work machines and is, thus, not limited to combine harvesters.

As shown in FIG. 1, agricultural harvester 100 illustratively includes an operator compartment 101, which can have a variety of different operator interface mechanisms, for controlling agricultural harvester 100. Agricultural harvester 100 includes front-end equipment, such as a header 102, and a cutter generally indicated at 104. Agricultural harvester 100 also includes a feeder house 106, a feed accelerator 108, and a thresher generally indicated at 110. The feeder house 106 and the feed accelerator 108 form part of a material handling subsystem 125. Header 102 is pivotally coupled to a frame 103 of agricultural harvester 100 along pivot axis 105. One or more actuators 107 drive movement of header 102 about axis 105 in the direction generally indicated by arrow 109. Thus, a vertical position of header 102 (the header height) above ground 111 over which the header 102 travels is controllable by actuating actuator 107. While not shown in FIG. 1, agricultural harvester 100 may also include one or more actuators that operate to apply a tilt angle, a roll angle, or both to the header 102 or portions of header 102. Tilt refers to an angle at which the cutter 104 engages the crop. The tilt angle is increased, for example, by controlling header 102 to point a distal edge 113 of cutter 104 more toward the ground. The tilt angle is decreased by controlling header 102 to point the distal edge 113 of cutter 104 more away from the ground. The roll angle refers to the orientation of header 102 about the front-to-back longitudinal axis of agricultural harvester 100.

Thresher 110 illustratively includes a threshing rotor 112 and a set of concaves 114. Further, agricultural harvester 100 also includes a separator 116. Agricultural harvester 100 also includes a cleaning subsystem or cleaning shoe (collectively referred to as cleaning subsystem 118) that includes a cleaning fan 120, chaffer 122, and sieve 124. The material handling subsystem 125 also includes discharge beater 126, tailings elevator 128, clean grain elevator 130, as well as unloading auger 134 and spout 136. The clean grain elevator moves clean grain into clean grain tank 132. Agricultural harvester 100 also includes a residue subsystem 138 that can include chopper 140 and spreader 142. Agricultural harvester 100 also includes a propulsion subsystem that includes an engine that drives ground engaging components 144, such as wheels or tracks. In some examples, a combine harvester within the scope of the present disclosure may have more than one of any of the subsystems mentioned above. In some examples, agricultural harvester 100 may have left and right cleaning subsystems, separators, etc., which are not shown in FIG. 1.

In operation, and by way of overview, agricultural harvester 100 illustratively moves through a field in the direction indicated by arrow 147. As agricultural harvester 100 moves, header 102 (and the associated reel 164) engages the crop to be harvested and gathers the crop toward cutter 104. An operator of agricultural harvester 100 can be a local human operator, a remote human operator, or an automated system. The operator of agricultural harvester 100 may determine one or more of a height setting, a tilt angle setting, or a roll angle setting for header 102. For example, the operator inputs a setting or settings to a control system, described in more detail below, that controls actuator 107. The control system may also receive a setting from the operator for establishing the tilt angle and roll angle of the header 102 and implement the inputted settings by controlling associated actuators, not shown, that operate to change the tilt angle and roll angle of the header 102. The actuator 107 maintains header 102 at a height above ground 111 based on a height setting and, where applicable, at desired tilt and roll angles. Each of the height, roll, and tilt settings may be implemented independently of the others. The control system responds to header error (e.g., the difference between the height setting and measured height of header 102 above ground 111 and, in some examples, tilt angle and roll angle errors) with a responsiveness that is determined based on a selected sensitivity level. If the sensitivity level is set at a greater level of sensitivity, the control system responds to smaller header position errors, and attempts to reduce the detected errors more quickly than when the sensitivity is at a lower level of sensitivity.

Returning to the description of the operation of agricultural harvester 100, after crops are cut by cutter 104, the severed crop material is moved through a conveyor in feeder house 106 toward feed accelerator 108, which accelerates the crop material into thresher 110. The crop material is threshed by rotor 112 rotating the crop against concaves 114. The threshed crop material is moved by a separator rotor in separator 116 where a portion of the residue is moved by discharge beater 126 toward the residue subsystem 138. The portion of residue transferred to the residue subsystem 138 is chopped by residue chopper 140 and spread on the field by spreader 142. In other configurations, the residue is released from the agricultural harvester 100 in a windrow. In other examples, the residue subsystem 138 can include weed seed eliminators (not shown) such as seed baggers or other seed collectors, or seed crushers or other seed destroyers.

Grain falls to cleaning subsystem 118. Chaffer 122 separates some larger pieces of material from the grain, and sieve 124 separates some of finer pieces of material from the clean grain. Clean grain falls to an auger that moves the grain to an inlet end of clean grain elevator 130, and the clean grain elevator 130 moves the clean grain upwards, depositing the clean grain in clean grain tank 132. Residue is removed from the cleaning subsystem 118 by airflow generated by cleaning fan 120. Cleaning fan 120 directs air along an airflow path upwardly through the sieves and chaffers. The airflow carries residue rearwardly in agricultural harvester 100 toward the residue handling subsystem 138.

Tailings elevator 128 returns tailings to thresher 110 where the tailings are re-threshed. Alternatively, the tailings also may be passed to a separate re-threshing mechanism by a tailings elevator or another transport device where the tailings are re-threshed as well.

FIG. 1 also shows that, in one example, agricultural harvester 100 includes ground speed sensor 146, one or more separator loss sensors 148, a clean grain camera 150, a forward looking image capture mechanism 151, which may be in the form of a stereo or mono camera, and one or more loss sensors 152 provided in the cleaning subsystem 118.

Ground speed sensor 146 senses the travel speed of agricultural harvester 100 over the ground. Ground speed sensor 146 may sense the travel speed of the agricultural harvester 100 by sensing the speed of rotation of the ground engaging components (such as wheels or tracks), a drive shaft, an axel, or other components. In some instances, the travel speed may be sensed using a positioning system, such as a global positioning system (GPS), a dead reckoning system, a long range navigation (LORAN) system, or a wide variety of other systems or sensors that provide an indication of travel speed.

Loss sensors 152 illustratively provide an output signal indicative of the quantity of grain loss occurring in both the right and left sides of the cleaning subsystem 118. In some examples, sensors 152 are strike sensors which count grain strikes per unit of time or per unit of distance traveled to provide an indication of the grain loss occurring at the cleaning subsystem 118. The strike sensors for the right and left sides of the cleaning subsystem 118 may provide individual signals or a combined or aggregated signal. In some examples, sensors 152 may include a single sensor as opposed to separate sensors provided for each cleaning subsystem 118.

Separator loss sensor 148 provides a signal indicative of grain loss in the left and right separators, not separately shown in FIG. 1. The separator loss sensors 148 may be associated with the left and right separators and may provide separate grain loss signals or a combined or aggregate signal. In some instances, sensing grain loss in the separators may also be performed using a wide variety of different types of sensors as well.

Agricultural harvester 100 may also include other sensors and measurement mechanisms. For instance, agricultural harvester 100 may include one or more of the following sensors: a header height sensor that senses a height of header 102 above ground 111; stability sensors that sense oscillation or bouncing motion (and amplitude) of agricultural harvester 100; a residue setting sensor that is configured to sense whether agricultural harvester 100 is configured to chop the residue, produce a windrow, etc.; a cleaning shoe fan speed sensor to sense the speed of cleaning fan 120; a concave clearance sensor that senses clearance between the rotor 112 and concaves 114; a threshing rotor speed sensor that senses a rotor speed of rotor 112; a chaffer clearance sensor that senses the size of openings in chaffer 122; a sieve clearance sensor that senses the size of openings in sieve 124; a material other than grain (MOG) moisture sensor that senses a moisture level of the MOG passing through agricultural harvester 100; one or more machine setting sensors configured to sense various configurable settings of agricultural harvester 100; a machine orientation sensor that senses the orientation of agricultural harvester 100; and crop property sensors that sense a variety of different types of crop properties, such as crop type, crop moisture, and other crop properties. Crop property sensors may also be configured to sense characteristics of the severed crop material as the crop material is being processed by agricultural harvester 100. For example, in some instances, the crop property sensors may sense grain quality such as broken grain, MOG levels; grain constituents such as starches and protein; and grain feed rate as the grain travels through the feeder house 106, clean grain elevator 130, or elsewhere in the agricultural harvester 100. The crop property sensors may also sense the feed rate of biomass through feeder house 106, through the separator 116 or elsewhere in agricultural harvester 100. The crop property sensors may also sense the feed rate as a mass flow rate of grain through elevator 130 or through other portions of the agricultural harvester 100 or provide other output signals indicative of other sensed variables. Crop property sensors can include one or more crop state sensors that sense crop state being harvested by agricultural harvester.

Crop state sensors can include a mono-camera or multi-camera system that captures one or more images of crop plants. For example, forward looking image capture mechanism 151 may form a crop state sensor that senses the crop state of crop plants in front of agricultural harvester 100. In another example, a crop state sensor can be placed on agricultural harvester 100 and view in one or more directions other than in front of agricultural harvester 100. Images captured by the crop state sensor can be analyzed to determine whether the crop is standing, has some magnitude of a down condition, is stubble, or is missing. Then, if the crop has some magnitude of a downed condition, then the image can be analyzed to determine the orientation of the downed crop. Some orientations can be relative to agricultural harvester 100, such as, but not limited to "sideways", "towards the machine", "away from the machine", or "random orientations." Some orientations can be absolute (e.g., relative to the earth) such as a numerical compass heading or numeric deviation from gravimetric or surface vertical in degrees. For example, in some instances, the orientation may be provided as a heading relative to magnetic north, relative to true north, relative to a crop row, relative to a harvester heading, or relative to other references.

In another example, a crop state sensor includes a range scanning device, such as, but not limited to radar, lidar, or sonar. A range scanning device can be used to sense the height of the crop. Crop height, while indicative of other things, can also indicate downed crop, the magnitude of a downed crop condition, or an orientation of the downed crop.

Prior to describing how agricultural harvester 100 generates a functional predictive crop state map and uses the functional predictive crop state map for presentation or control, a brief description of some of the items on agricultural harvester 100, and their respective operations, will first be described. The description of FIGS. 2 and 3 describe receiving a general type of information map and combining information from the information map with a georeferenced sensor signal generated by an in-situ sensor, where the sensor signal is indicative of a characteristic in the field, such as characteristics of crop or weeds present in the field. Characteristics of the field may include, but are not limited to, characteristics of a field such as slope, weed intensity, weed type, soil moisture, surface quality; characteristics of crop properties such as crop height, crop moisture, crop density, crop state; characteristics of grain properties such as grain moisture, grain size, grain test weight; and characteristics of machine performance such as loss levels, job quality, fuel consumption, and power utilization. A relationship between the characteristic values obtained from in-situ sensor signals and the information map values is identified, and that relationship is used to generate a new functional predictive map. A functional predictive map predicts values at different geographic locations in a field, and one or more of those values may be used for controlling a machine, such as one or more subsystems of an agricultural harvester. In some instances, a functional predictive map can be presented to a user, such as an operator of an agricultural work machine, which may be an agricultural harvester. A functional predictive map may be presented to a user visually, such as via a display, haptically, or audibly. The user may interact with the functional predictive map to perform editing operations and other user interface operations. In some instances, a functional predictive map can be used for one or more of controlling an agricultural work machine, such as an agricultural harvester, presentation to an operator or other user, and presentation to an operator or user for interaction by the operator or user.

Figure 2:
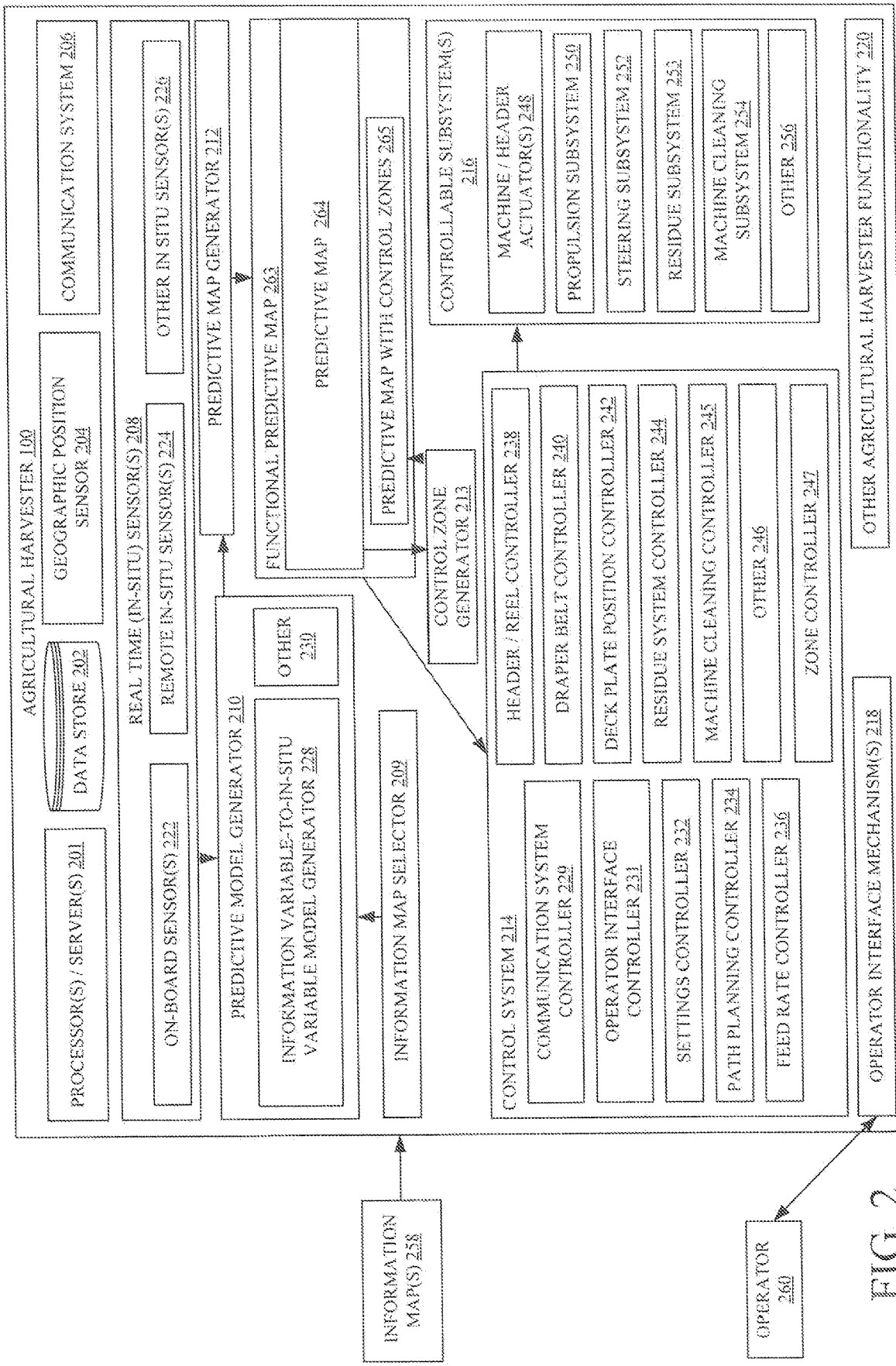
FIG. 2 is a block diagram showing some portions of an agricultural harvester in more detail, according to some examples of the present disclosure.
Figure 3A:
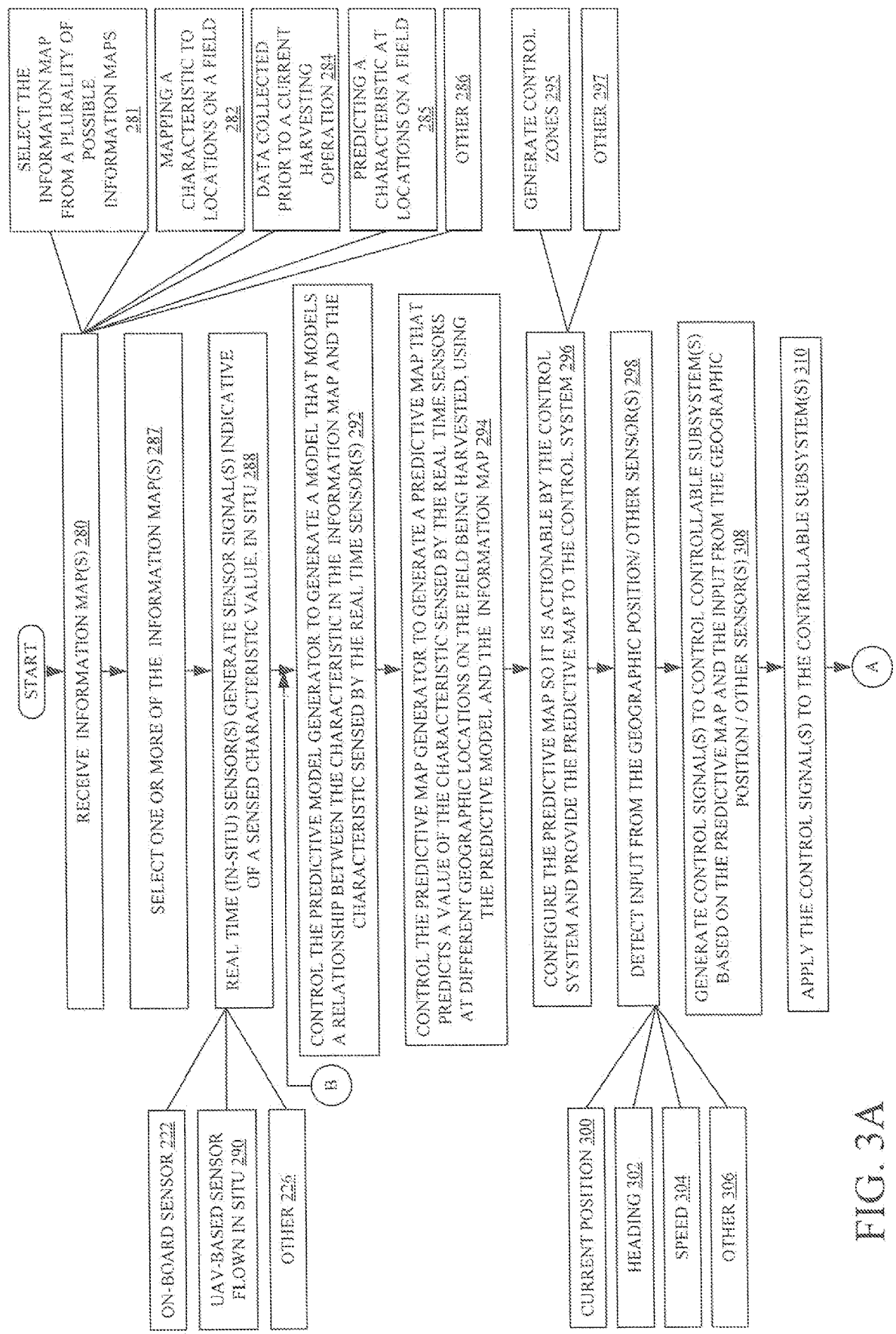
FIGS. 3A-3B (collectively referred to herein as FIG. 3) show a flow diagram illustrating an example of operation of an agricultural harvester in generating a map.
Figure 3B:
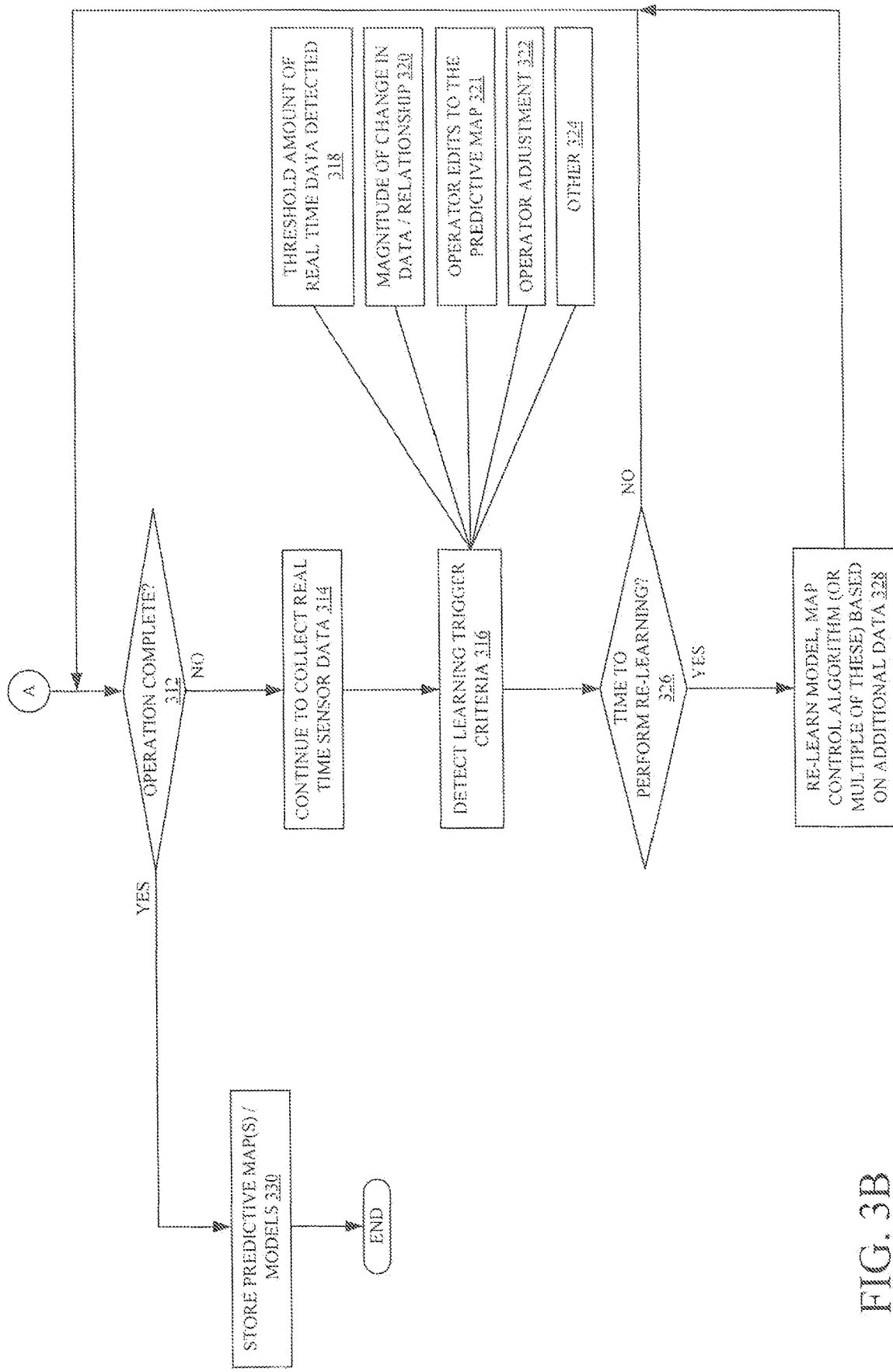
Figure 4:
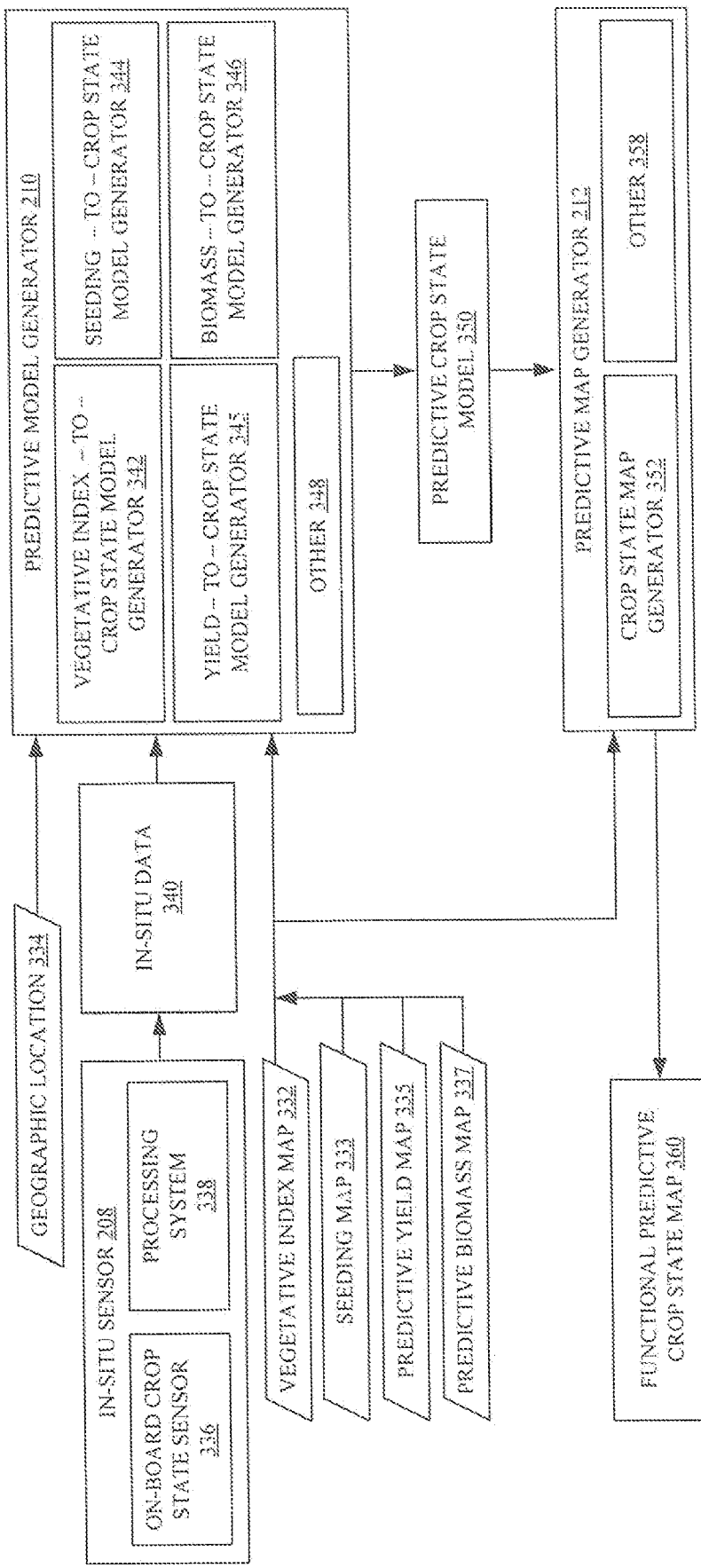
FIG. 4 is a block diagram showing one example of a predictive model generator and a predictive map generator.
Figure 5:
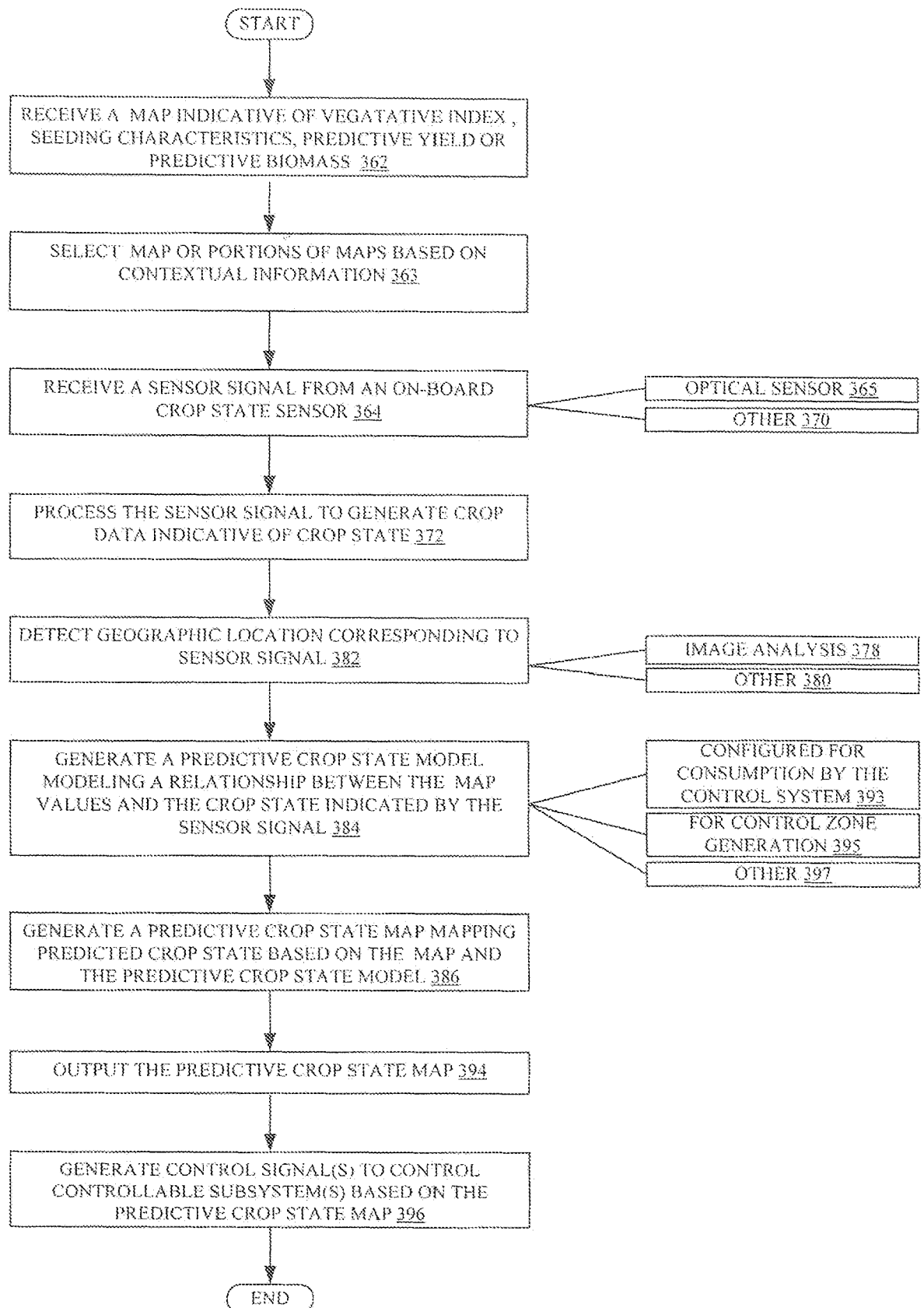
FIG. 5 is a flow diagram showing an example of operation of an agricultural harvester in receiving a vegetative index, seeding characteristic, predictive yield, or predictive biomass map; detecting an in-situ crop state characteristic; and generating a functional predictive crop state map for presentation or use in controlling the agricultural harvester during a harvesting operation or both.

After a general approach is described with respect to FIGS. 2 and 3, a more specific approach for generating a functional predictive crop state map that can be presented to an operator or user, or used to control agricultural harvester 100, or both is described with respect to FIGS. 4 and 5. Again, while the present discussion proceeds with respect to the agricultural harvester and, particularly, a combine harvester, the scope of the present disclosure encompasses other types of agricultural harvesters or other agricultural work machines.

FIG. 2 is a block diagram showing some portions of an example agricultural harvester 100. FIG. 2 shows that agricultural harvester 100 illustratively includes one or more processors or servers 201, data store 202, geographic position sensor 204, communication system 206, and one or more in-situ sensors 208 that sense one or more agricultural characteristics of a field concurrent with a harvesting operation. An agricultural characteristic can include any characteristic that can have an effect of the harvesting operation. Some examples of agricultural characteristics include characteristics of the harvesting machine, the field, the plants on the field, and the weather. Other types of agricultural characteristics are also included. The in-situ sensors 208 generate values corresponding to the sensed characteristics. The agricultural harvester 100 also includes a predictive model or relationship generator (collectively referred to hereinafter as "predictive model generator 210"), predictive map generator 212, control zone generator 213, control system 214, one or more controllable subsystems 216, and an operator interface mechanism 218. The agricultural harvester 100 can also include a wide variety of other agricultural harvester functionality 220. The in-situ sensors 208 include, for example, on-board sensors 222, remote sensors 224, and other sensors 226 that sense characteristics of a field during the course of an agricultural operation. Predictive model generator 210 illustratively includes an information variable-to-in-situ variable model generator 228, and predictive model generator 210 can include other items 230. Control system 214 includes communication system controller 229, operator interface controller 231, a settings controller 232, path planning controller 234, feed rate controller 236, header and reel controller 238, draper belt controller 240, deck plate position controller 242, residue system controller 244, machine cleaning controller 245, zone controller 247, and control system 214 can include other items 246. Controllable subsystems 216 include machine and header actuators 248, propulsion subsystem 250, steering subsystem 252, residue subsystem 138, machine cleaning subsystem 254, and controllable subsystems 216 can include a wide variety of other subsystems 256.

FIG. 2 also shows that agricultural harvester 100 can receive one or more information maps 258. As described below, an information map 258 includes, for example, a vegetative index, seeding characteristic, predictive yield, or predictive biomass map. However, information map 258 may also encompass other types of data that were obtained prior to a harvesting operation, such as contextual information. Contextual information can include, without limitation, one or more of weather conditions over part of or all of a growing season, presence of pests, geographic location, soil types, irrigation, treatment application, etc. Weather conditions can include, without limitation, precipitation over the season, presence of hail capable of crop damage, presence of high winds, direction of high winds, temperature over the season, etc. Some examples of pests broadly include, insects, fungi, weeds, bacteria, viruses, etc. Some examples of treatment applications include herbicide, pesticide, fungicide, fertilizer, mineral supplements, etc. FIG. 2 also shows that an operator 260 may operate the agricultural harvester 100. The operator 260 interacts with operator interface mechanisms 218. In some examples, operator interface mechanisms 218 may include joysticks, levers, a steering wheel, linkages, pedals, buttons, dials, keypads, user actuatable elements (such as icons, buttons, etc.) on a user interface display device, a microphone and speaker (where speech recognition and speech synthesis are provided), among a wide variety of other types of control devices. Where a touch sensitive display system is provided, operator 260 may interact with operator interface mechanisms 218 using touch gestures. These examples described above are provided as illustrative examples and are not intended to limit the scope of the present disclosure. Consequently, other types of operator interface mechanisms may be used and are within the scope of the present disclosure.

Information map 258 may be downloaded onto agricultural harvester 100 and stored in data store 202, using communication system 206 or in other ways. In some examples, communication system 206 may be a cellular communication system, a system for communicating over a wide area network or a local area network, a system for communicating over a near field communication network, or a communication system configured to communicate over any of a variety of other networks or combinations of networks. Communication system 206 may also include a system that facilitates downloads or transfers of information to and from a secure digital (SD) card or a universal serial bus (USB) card, or both.

Geographic position sensor 204 illustratively senses or detects the geographic position or location of agricultural harvester 100. Geographic position sensor 204 can include, but is not limited to, a global navigation satellite system (GNSS) receiver that receives signals from a GNSS satellite transmitter. Geographic position sensor 204 can also include a real-time kinematic (RTK) component that is configured to enhance the precision of position data derived from the GNSS signal. Geographic position sensor 204 can include a dead reckoning system, a cellular triangulation system, or any of a variety of other geographic position sensors.

In-situ sensors 208 may be any of the sensors described above with respect to FIG. 1. In-situ sensors 208 include on-board sensors 222 that are mounted on-board agricultural harvester 100. Such sensors may include, for instance, a perception, image, or optical sensor, such as, a forward looking mono or stereo camera system and image processing system or cameras mounted to view crop plants proximate to agricultural harvester 100 other than forward of agricultural harvester 100. The in-situ sensors 208 may also include remote in-situ sensors 224 that capture in-situ information. In-situ data include data taken from a sensor on-board the agricultural harvester or taken by any sensor where the data are detected during the harvesting operation.

Predictive model generator 210 generates a model that is indicative of a relationship between the values sensed by the in-situ sensor 208 and a characteristic mapped to the field by the information map 258. For example, if the information map 258 maps a vegetative index value to different locations in the field and the in-situ sensor 208 is sensing a value indicative of crop state, then information variable-to-in-situ variable model generator 228 generates a predictive crop state model that models the relationship between the vegetative index values and the crop state values. Predictive map generator 212 uses the predictive crop state model generated by predictive model generator 210 to generate a functional predictive crop state map that predicts the value of crop state, at different locations in the field based upon the information map 258. Predictive map generator 212 can use the vegetative index values in information map 258 and the model generated by predictive model generator 210 to generate a functional predictive map 263 that predicts the crop state at different locations in the field. Predictive map generator 212 thus outputs predictive map 264.

Or for example, if the information map 258 maps a seeding characteristic to different locations in the field and the in-situ sensor 208 is sensing a value indicative of crop state, then information variable-to-in-situ variable model generator 228 generates a predictive crop state model that models the relationship between the seeding characteristics (with or without contextual information) and the in-situ crop state values. Predictive map generator 212 uses the predictive crop state model generated by predictive model generator 210 to generate a functional predictive crop state map that predicts the value of crop state that will be sensed by the in-situ sensors 208, at different locations in the field based upon the information map 258. Predictive map generator 212 can use the seeding characteristic values in information map 258 and the model generated by predictive model generator 210 to generate a functional predictive map 263 that predicts the crop state at different locations in the field. Predictive map generator 212 thus outputs predictive map 264.

In some examples, the type of data in the functional predictive map 263 may be the same as the in-situ data type sensed by the in-situ sensors 208. In some instances, the type of data in the functional predictive map 263 may have different units from the data sensed by the in-situ sensors 208. In some examples, the type of data in the functional predictive map 263 may be different from the data type sensed by the in-situ sensors 208 but has a relationship to data type sensed by the in-situ sensors 208. For example, in some examples, the in-situ data type may be indicative of the type of data in the functional predictive map 263. In some examples, the type of data in the functional predictive map 263 may be different than the data type in the information map 258. In some instances, the type of data in the functional predictive map 263 may have different units from the data in the information map 258. In some examples, the type of data in the functional predictive map 263 may be different from the data type in the information map 258 but has a relationship to the data type in the information map 258. For example, in some examples, the data type in the information map 258 may be indicative of the type of data in the functional predictive map 263. In some examples, the type of data in the functional predictive map 263 is different than one of, or both of the in-situ data type sensed by the in-situ sensors 208 and the data type in the information map 258. In some examples, the type of data in the functional predictive map 263 is the same as one of, or both of, of the in-situ data type sensed by the in-situ sensors 208 and the data type in information map 258. In some examples, the type of data in the functional predictive map 263 is the same as one of the in-situ data type sensed by the in-situ sensors 208 or the data type in the information map 258, and different than the other.

As shown in FIG. 2, predictive map 264 predicts the value of a characteristic sensed by in-situ sensors 208, or a characteristic related to the characteristic sensed by in-situ sensors 208 at various locations across the field based upon an information value in information map 258 at those locations (or locations with similar contextual information) and using the predictive model 350. For example, if predictive model generator 210 has generated a predictive model indicative of a relationship between a vegetative index value and crop state, then, given the vegetative index value at different locations across the field, predictive map generator 212 generates a predictive map 264 that predicts the value of the crop state at different locations across the field. The vegetative index value at those locations obtained from the information map 258 and the relationship between vegetative index value and crop state obtained from the predictive model 350 are used to generate the predictive map 264.

Some variations in the data types that are mapped in the information map 258, the data types sensed by in-situ sensors 208 and the data types predicted on the predictive map 264 will now be described.

In some examples, the data type in the information map 258 is different from the data type sensed by in-situ sensors 208, yet the data type in the predictive map 264 is the same as the data type sensed by the in-situ sensors 208. For instance, the information map 258 may be a vegetative index map, and the variable sensed by the in-situ sensors 208 may be crop state. The predictive map 264 may then be a predictive crop state map that maps predicted crop state values to different geographic locations in the field. In another example, the information map 258 may be a vegetative index map, and the variable sensed by the in-situ sensors 208 may be crop height. The predictive map 264 may then be a predictive crop height map that maps predicted crop height values to different geographic locations in the field.

Also, in some examples, the data type in the information map 258 is different from the data type sensed by in-situ sensors 208, and the data type in the predictive map 264 is different from both the data type in the information map 258 and the data type sensed by the in-situ sensors 208. For instance, the information map 258 may be a vegetative index map, and the variable sensed by the in-situ sensors 208 may be crop height. The predictive map 264 may then be a predictive biomass map that maps predicted biomass values to different geographic locations in the field. In another example, the information map 258 may be a vegetative index map, and the variable sensed by the in-situ sensors 208 may be crop state. The predictive map 264 may then be a predictive speed map that maps predicted harvester speed values to different geographic locations in the field.

In some examples, the information map 258 is from a prior pass through the field during a prior operation and the data type is different from the data type sensed by in-situ sensors 208, yet the data type in the predictive map 264 is the same as the data type sensed by the in-situ sensors 208. For instance, the information map 258 may be a seed population map generated during planting, and the variable sensed by the in-situ sensors 208 may be stalk size. The predictive map 264 may then be a predictive stalk size map that maps predicted stalk size values to different geographic locations in the field. In another example, the information map 258 may be a seeding genotype map, and the variable sensed by the in-situ sensors 208 may be crop state such as standing crop or down crop. The predictive map 264 may then be a predictive crop state map that maps predicted crop state values to different geographic locations in the field.

In some examples, the information map 258 is from a prior pass through the field during a prior operation and the data type is the same as the data type sensed by in-situ sensors 208, and the data type in the predictive map 264 is also the same as the data type sensed by the in-situ sensors 208. For instance, the information map 258 may be a yield map generated during a previous year, and the variable sensed by the in-situ sensors 208 may be yield. The predictive map 264 may then be a predictive yield map that maps predicted yield values to different geographic locations in the field. In such an example, the relative yield differences in the georeferenced information map 258 from the prior year can be used by predictive model generator 210 to generate a predictive model that models a relationship between the relative yield differences on the information map 258 and the yield values sensed by in-situ sensors 208 during the current harvesting operation. The predictive model is then used by predictive map generator 212 to generate a predictive yield map.

In another example, the information map 258 may be a weed intensity map generated during a prior operation, such as from a sprayer, and the variable sensed by the in-situ sensors 208 may be weed intensity. The predictive map 264 may then be a predictive weed intensity map that maps predicted weed intensity values to different geographic locations in the field. In such an example, a map of the weed intensities at time of spraying is georeferenced recorded and provided to agricultural harvester 100 as an information map 258 of weed intensity. In-situ sensors 208 can detect weed intensity at geographic locations in the field and predictive model generator 210 may then build a predictive model that models a relationship between weed intensity at time of harvest and weed intensity at time of spraying. This is because the sprayer will have impacted the weed intensity at time of spraying, but weeds may still crop up in similar areas again by harvest. However, the weed areas at harvest are likely to have different intensity based on timing of the harvest, weather, weed type, among other things.

In some examples, predictive map 264 can be provided to the control zone generator 213. Control zone generator 213 groups adjacent portions of an area into one or more control zones based on data values of predictive map 264, that are associated with those adjacent portions. A control zone may include two or more contiguous portions of an area, such as a field, for which a control parameter corresponding to the control zone for controlling a controllable subsystem is constant. For example, a response time to alter a setting of controllable subsystems 216 may be inadequate to satisfactorily respond to changes in values contained in a map, such as predictive map 264. In that case, control zone generator 213 parses the map and identifies control zones that are of a defined size to accommodate the response time of the controllable subsystems 216. In another example, control zones may be sized to reduce wear from excessive actuator movement resulting from continuous adjustment. In some examples, there may be a different set of control zones for each controllable subsystem 216 or for groups of controllable subsystems 216. The control zones may be added to the predictive map 264 to obtain predictive control zone map 265. Predictive control zone map 265 can thus be similar to predictive map 264 except that predictive control zone map 265 includes control zone information defining the control zones. Thus, a functional predictive map 263, as described herein, may or may not include control zones. Both predictive map 264 and predictive control zone map 265 are functional predictive maps 263. In one example, a functional predictive map 263 does not include control zones, such as predictive map 264. In another example, a functional predictive map 263 does include control zones, such as predictive control zone map 265. In some examples, multiple crops may be simultaneously present in a field if an intercrop production system is implemented. In that case, predictive map generator 212 and control zone generator 213 are able to identify the location and characteristics of the two or more crops and then generate predictive map 264 and predictive control zone map 265 with control zones accordingly.

It will also be appreciated that control zone generator 213 can cluster values to generate control zones and the control zones can be added to predictive control zone map 265, or a separate map, showing only the control zones that are generated. In some examples, the control zones may be used for controlling or calibrating agricultural harvester 100 or both. In other examples, the control zones may be presented to the operator 260 and used to control or calibrate agricultural harvester 100, and, in other examples, the control zones may be presented to the operator 260 or another user or stored for later use.

Predictive map 264 or predictive control zone map 265 or both are provided to control system 214, which generates control signals based upon the predictive map 264 or predictive control zone map 265 or both. In some examples, communication system controller 229 controls communication system 206 to communicate the predictive map 264 or predictive control zone map 265 or control signals based on the predictive map 264 or predictive control zone map 265 to other agricultural harvesters that are harvesting in the same field. In some examples, communication system controller 229 controls the communication system 206 to send the predictive map 264, predictive control zone map 265, or both to other remote systems.

Operator interface controller 231 is operable to generate control signals to control operator interface mechanisms 218. The operator interface controller 231 is also operable to present the predictive map 264 or predictive control zone map 265 or other information derived from or based on the predictive map 264, predictive control zone map 265, or both to operator 260. Operator 260 may be a local operator or a remote operator. As an example, controller 231 generates control signals to control a display mechanism to display one or both of predictive map 264 and predictive control zone map 265 for the operator 260. Controller 231 may generate operator actuatable mechanisms that are displayed and can be actuated by the operator to interact with the displayed map. The operator can edit the map by, for example, correcting a crop state value displayed on the map based, for instance, on the operator's observation. Settings controller 232 can generate control signals to control various settings on the agricultural harvester 100 based upon predictive map 264, the predictive control zone map 265, or both. For instance, settings controller 232 can generate control signals to control machine and header actuators 248. In response to the generated control signals, the machine and header actuators 248 operate to control, for example, one or more of the sieve and chaffer settings, thresher clearance, rotor settings, cleaning fan speed settings, header height, header functionality, reel speed, reel position, draper functionality (where agricultural harvester 100 is coupled to a draper header), corn header functionality, internal distribution control, and other actuators 248 that affect the other functions of the agricultural harvester 100. Path planning controller 234 illustratively generates control signals to control steering subsystem 252 to steer agricultural harvester 100 according to a desired path. Path planning controller 234 can control a path planning system to generate a route for agricultural harvester 100 and can control propulsion subsystem 250 and steering subsystem 252 to steer agricultural harvester 100 along that route. Feed rate controller 236 can control various subsystems, such as propulsion subsystem 250 and machine actuators 248, to control a feed rate based upon the predictive map 264 or predictive control zone map 265 or both. For instance, as agricultural harvester 100 approaches an area containing crop having a downed crop condition that is greater than a selected threshold, feed rate controller 236 may reduce the speed of agricultural harvester 100 to ensure that crop feeding performance is acceptable and that the crop material is gathered. Header and reel controller 238 can generate control signals to control a header or a reel or other header functionality. For example, in an area of down crop, it may be beneficial to adjust header height or reel positions. Draper belt controller 240 can generate control signals to control a draper belt or other draper functionality based upon the predictive map 264, predictive control zone map 265, or both. Deck plate position controller 242 can generate control signals to control a position of a deck plate included on a header based on predictive map 264 or predictive control zone map 265 or both, and residue system controller 244 can generate control signals to control a residue subsystem 138 based upon predictive map 264 or predictive control zone map 265, or both. Machine cleaning controller 245 can generate control signals to control machine cleaning subsystem 254. For instance, based upon the different types of seeds or weeds passed through agricultural harvester 100, a particular type of machine cleaning operation or a frequency with which a cleaning operation is performed may be controlled. Other controllers included on the agricultural harvester 100 can control other subsystems based on the predictive map 264 or predictive control zone map 265 or both as well.

FIGS. 3A and 3B (collectively referred to herein as FIG. 3) show a flow diagram illustrating one example of the operation of agricultural harvester 100 in generating a predictive map 264 and predictive control zone map 265 based upon information map 258.

At 280, agricultural harvester 100 receives information map 258. Examples of information map 258 or receiving information map 258 are discussed with respect to blocks

282, 284, 285 and 286. As discussed above, information map 258 maps values of a variable, corresponding to a first characteristic, to different locations in the field, as indicated at block 282. As indicated at block 281, receiving the information map 258 may involve selecting one or more of a plurality of possible information maps that are available. For instance, one information map may be a vegetative index map generated from aerial imagery. Another information map may be a map generated during a prior pass through the field which may have been performed by a different machine performing a previous operation in the field, such as a sprayer or other machine. The process by which one or more information maps are selected can be manual, semi-automated, or automated. The information map 258 is based on data collected prior to a current harvesting operation. This is indicated by block 284. For instance, the data may be collected based on aerial images or the data may be measured values taken during a previous year, earlier in the current growing season, or at other times. The information may be based on data detected in other ways (other than using aerial images) as well. For instance, information map 258 can be transmitted to agricultural harvester 100 using communication system 206 and stored in data store 202.

The information map 258 can be a predictive map as well, this is indicated by block 285. As indicated above the predictive map may include a predictive yield map or a predictive biomass map generated based, for example, in part on a prior vegetative index map or other information map and in-situ sensor values. In some examples, a predictive yield map or a predictive biomass map may be based in whole or in part on a topographic map, a soil type map, a soil constituent map, or a soil health map. The predictive yield or biomass map can be predicted and generated in other ways as well.

Information map 258 can be loaded onto agricultural harvester 100 using communication system 206 in other ways as well, and this is indicated by block 286 in the flow diagram of FIG. 3. In some examples, the information map 258 can be received by communication system 206.

Upon commencement of a harvesting operation, in-situ sensors 208 generate sensor signals indicative of one or more in-situ data values indicative of a plant characteristic, such as a crop state, as indicated by block 288. Examples of in-situ sensors 288 are discussed with respect to blocks 222, 290, and 226. As explained above, the in-situ sensors 208 include on-board sensors 222; remote in-situ sensors 224, such as UAV-based sensors flown at a time to gather in-situ data, shown in block 290; or other types of in-situ sensors, designated by in-situ sensors 226. In some examples, data from on-board sensors is georeferenced using position heading or speed data from geographic position sensor 204.

Predictive model generator 210 controls the information variable-to-in-situ variable model generator 228 to generate a model that models a relationship between the mapped values contained in the information map 258 and the in-situ values sensed by the in-situ sensors 208 as indicated by block 292. The characteristics or data types represented by the mapped values in the information map 258 and the in-situ values sensed by the in-situ sensors 208 may be the same characteristics or data type or different characteristics or data types.

The relationship or model generated by predictive model generator 210 is provided to predictive map generator 212. Predictive map generator 212 generates a predictive map 264 that predicts a value of the characteristic sensed by the in-situ sensors 208 at different geographic locations in a field being harvested, or a different characteristic that is related to the characteristic sensed by the in-situ sensors 208, using the predictive model and the information map 258, as indicated by block 294.

It should be noted that, in some examples, the information map 258 may include two or more different maps or two or more different map layers of a single map. Each map layer may represent a different data type from the data type of another map layer or the map layers may have the same data type that were obtained at different times. Each map in the two or more different maps or each layer in the two or more different map layers of a map maps a different type of variable to the geographic locations in the field. In such an example, predictive model generator 210 generates a predictive model that models the relationship between the in-situ data and each of the different variables mapped by the two or more different maps or the two or more different map layers. Similarly, the in-situ sensors 208 can include two or more sensors each sensing a different type of variable. Thus, the predictive model generator 210 generates a predictive model that models the relationships between each type of variable mapped by the information map 258 and each type of variable sensed by the in-situ sensors 208. Predictive map generator 212 can generate a functional predictive map 263 that predicts a value for each sensed characteristic sensed by the in-situ sensors 208 (or a characteristic related to the sensed characteristic) at different locations in the field being harvested using the predictive model and each of the maps or map layers in the information map 258.

Predictive map generator 212 configures the predictive map 264 so that the predictive map 264 is actionable (or consumable) by control system 214. Predictive map generator 212 can provide the predictive map 264 to the control system 214 or to control zone generator 213 or both. Some examples of different ways in which the predictive map 264 can be configured or output are described with respect to blocks 296, 295, 299 and 297. For instance, predictive map generator 212 configures predictive map 264 so that predictive map 264 includes values that can be read by control system 214 and used as the basis for generating control signals for one or more of the different controllable subsystems of the agricultural harvester 100, as indicated by block 296.

Control zone generator 213 can divide the predictive map 264 into control zones based on the values on the predictive map 264. Contiguously-geolocated values that are within a threshold value of one another can be grouped into a control zone. The threshold value can be a default threshold value, or the threshold value can be set based on an operator input, based on an input from an automated system, or based on other criteria. A size of the zones may be based on a responsiveness of the control system 214, the controllable subsystems 216, based on wear considerations, or on other criteria as indicated by block 295. Predictive map generator 212 configures predictive map 264 for presentation to an operator or other user. Control zone generator 213 can configure predictive control zone map 265 for presentation to an operator or other user. This is indicated by block 299. When presented to an operator or other user, the presentation of the predictive map 264 or predictive control zone map 265 or both may contain one or more of the predictive values on the predictive map 264 correlated to geographic location, the control zones on predictive control zone map 265 correlated to geographic location, and settings values or control parameters that are used based on the predicted values on predictive map 264 or zones on predictive control zone map 265. The presentation can, in another example, include more abstracted information or more detailed information. The presentation can also include a confidence level that indicates an accuracy with which the predictive values on predictive map 264 or the zones on predictive control zone map 265 conform to measured values that may be measured by sensors on agricultural harvester 100 as agricultural harvester 100 moves through the field. Further where information is presented to more than one location, an authentication and authorization system can be provided to implement authentication and authorization processes. For instance, there may be a hierarchy of individuals that are authorized to view and change maps and other presented information. By way of example, an on-board display device may show the maps in near real time locally on the machine, or the maps may also be generated at one or more remote locations, or both. In some examples, each physical display device at each location may be associated with a person or a user permission level. The user permission level may be used to determine which display elements are visible on the physical display device and which values the corresponding person may change. As an example, a local operator of agricultural harvester 100 may be unable to see the information corresponding to the predictive map 264 or make any changes to machine operation. A supervisor, such as a supervisor at a remote location, however, may be able to see the predictive map 264 on the display but be prevented from making any changes. A manager, who may be at a separate remote location, may be able to see all of the elements on predictive map 264 and also be able to change the predictive map 264. In some instances, the predictive map 264 accessible and changeable by a manager located remotely may be used in machine control. This is one example of an authorization hierarchy that may be implemented. The predictive map 264 or predictive control zone map 265 or both can be configured in other ways as well, as indicated by block 297.

At block 298, input from geographic position sensor 204 and other in-situ sensors 208 are received by the control system. Particularly, at block 300, control system 214 detects an input from the geographic position sensor 204 identifying a geographic location of agricultural harvester 100. Block 302 represents receipt by the control system 214 of sensor inputs indicative of trajectory or heading of agricultural harvester 100, and block 304 represents receipt by the control system 214 of a speed of agricultural harvester 100. Block 306 represents receipt by the control system 214 of other information from various in-situ sensors 208.

At block 308, control system 214 generates control signals to control the controllable subsystems 216 based on the predictive map 264 or predictive control zone map 265 or both and the input from the geographic position sensor 204 and any other in-situ sensors 208. At block 310, control system 214 applies the control signals to the controllable subsystems. It will be appreciated that the particular control signals that are generated, and the particular controllable subsystems 216 that are controlled, may vary based upon one or more different things. For example, the control signals that are generated and the controllable subsystems 216 that are controlled may be based on the type of predictive map 264 or predictive control zone map 265 or both that is being used. Similarly, the control signals that are generated and the controllable subsystems 216 that are controlled and the timing of the control signals can be based on various latencies of crop flow through the agricultural harvester 100 and the responsiveness of the controllable subsystems 216.

By way of example, a generated predictive map 264 in the form of a predictive crop state map can be used to control one or more controllable subsystems 216. For example, the functional predictive crop state map can include crop state values georeferenced to locations within the field being harvested. The functional predictive crop state map can be extracted and used to control, for example, the steering and propulsion subsystems 252 and 250. By controlling the steering and propulsion subsystems 252 and 250, a feed rate of material or grain moving through the agricultural harvester 100 can be controlled. Or for example, by controlling the steering and propulsion subsystems 252 and 250, a direction opposite the direction the crop is leaning of the downed crop can be maintained. Similarly, the header height can be controlled to take in more or less material (in some cases the header has to be lowered to ensure crop is contacted) and thus the header height can also be controlled to control feed rate of material through the agricultural harvester 100. In other examples, if the predictive map 264 maps a crop state forward of the machine in which crop is in a downed condition along one portion of the header and not on another portion of the header or if crop is in a downed condition to a greater extent along one portion of the header compared to another portion of the header, the header can be controlled to tilt, roll, or both to gather the downed crop in a more effective manner. The preceding examples involving feed rate and header control using a functional predictive crop state map is provided merely as an example. Consequently, a wide variety of other control signals can be generated using values obtained from a predictive crop state map or other type of functional predictive map to control one or more of the controllable subsystems 216.

At block 312, a determination is made as to whether the harvesting operation has been completed. If harvesting is not completed the processing advances to block 314 where in-situ sensor data from geographic position sensor 204 and in-situ sensors 208 (and perhaps other sensors) continue to be read.

In some examples, at block 316, agricultural harvester 100 can also detect learning trigger criteria to perform machine learning on one or more of the predictive map 264, predictive control zone map 265, the model generated by predictive model generator 210, the zones generated by control zone generator 213, one or more control algorithms implemented by the controllers in the control system 214, and other triggered learning.

The learning trigger criteria can include any of a wide variety of different criteria. Some examples of detecting trigger criteria are discussed with respect to blocks 318, 320, 321, 322 and 324. For instance, in some examples, triggered learning can involve recreation of a relationship used to generate a predictive model when a threshold amount of in-situ sensor data are obtained from in-situ sensors 208. In such examples, receipt of an amount of in-situ sensor data from the in-situ sensors 208 that exceeds a threshold triggers or causes the predictive model generator 210 to generate a new predictive model that is used by predictive map generator 212. Thus, as agricultural harvester 100 continues a harvesting operation, receipt of the threshold amount of in-situ sensor data from the in-situ sensors 208 triggers the creation of a new relationship represented by a predictive model generated by predictive model generator 210. Further, new predictive map 264, predictive control zone map 265, or both can be regenerated using the new predictive model. Block 318 represents detecting a threshold amount of in-situ sensor data used to trigger creation of a new predictive model.

In other examples, the learning trigger criteria may be based on how much the in-situ sensor data from the in-situ sensors 208 are changing, such as over time or compared to previous values. For example, if variations within the in-situ sensor data (or the relationship between the in-situ sensor data and the information in information map 258) are within a selected range or is less than a defined amount, or below a threshold value, then a new predictive model is not generated by the predictive model generator 210. As a result, the predictive map generator 212 does not generate a new predictive map 264, predictive control zone map 265, or both. However, if variations within the in-situ sensor data are outside of the selected range, are greater than the defined amount, or are above the threshold value, for example, then the predictive model generator 210 generates a new predictive model using all or a portion of the newly received in-situ sensor data that the predictive map generator 212 uses to generate a new predictive map 264. At block 320, variations in the in-situ sensor data, such as a magnitude of an amount by which the data exceeds the selected range or a magnitude of the variation of the relationship between the in-situ sensor data and the information in the information map 258, can be used as a trigger to cause generation of a new predictive model and predictive map. Keeping with the examples described above, the threshold, the range, and the defined amount can be set to default values; set by an operator or user interaction through a user interface; set by an automated system; or set in other ways.

Other learning trigger criteria can also be used. For instance, if predictive model generator 210 switches to a different information map (different from the originally selected information map 258), then switching to the different information map may trigger re-learning by predictive model generator 210, predictive map generator 212, control zone generator 213, control system 214, or other items. In another example, transitioning of agricultural harvester 100 to a different topography or to a different control zone may be used as learning trigger criteria as well.

In some instances, operator 260 can also edit the predictive map 264 or predictive control zone map 265 or both. The edits can change a value on the predictive map 264 or, change a size, shape, position or existence of a control zone on predictive control zone map 265, or both. Block 321 shows that edited information can be used as learning trigger criteria.

In some instances, it may also be that operator 260 observes that automated control of a controllable subsystem, is not what the operator desires. In such instances, the operator 260 may provide a manual adjustment to the controllable subsystem reflecting that the operator 260 desires the controllable subsystem to operate in a different way than is being commanded by control system 214. Thus, manual alteration of a setting by the operator 260 can cause one or more of predictive model generator 210 to relearn a model, predictive map generator 212 to regenerate map 264, control zone generator 213 to regenerate one or more control zones on predictive control zone map 265, and control system 214 to relearn a control algorithm or to perform machine learning on one or more of the controller components 232 through 246 in control system 214 based upon the adjustment by the operator 260, as shown in block 322. Block 324 represents the use of other triggered learning criteria.

In other examples, relearning may be performed periodically or intermittently based, for example, upon a selected time interval such as a discrete time interval or a variable time interval, as indicated by block 326.

If relearning is triggered, whether based upon learning trigger criteria or based upon passage of a time interval, as indicated by block 326, then one or more of the predictive model generator 210, predictive map generator 212, control zone generator 213, and control system 214 performs machine learning to generate a new predictive model, a new predictive map, a new control zone, and a new control algorithm, respectively, based upon the learning trigger criteria. The new predictive model, the new predictive map, and the new control algorithm are generated using any additional data that has been collected since the last learning operation was performed. Performing relearning is indicated by block 328.

If the harvesting operation has been completed, operation moves from block 312 to block 330 where one or more of the predictive map 264, predictive control zone map 265, and predictive model generated by predictive model generator 210 are stored. The predictive map 264, predictive control zone map 265, and predictive model may be stored locally on data store 202 or sent to a remote system using communication system 206 for later use.

It will be noted that while some examples herein describe predictive model generator 210 and predictive map generator 212 receiving an information map in generating a predictive model and a functional predictive map, respectively, in other examples, the predictive model generator 210 and predictive map generator 212 can receive, in generating a predictive model and a functional predictive map, respectively other types of maps, including predictive maps, such as a functional predictive map generated during the harvesting operation.

FIG. 4 is a block diagram of a portion of the agricultural harvester 100 shown in FIG. 1. Particularly, FIG. 4 shows, among other things, examples of the predictive model generator 210 and the predictive map generator 212 in more detail. FIG. 4 also illustrates information flow among the various components shown therein. As shown, the predictive model generator 210 receives one or more of a vegetative index map 332, a seeding characteristic map 333, a predictive yield map 335, or a predictive biomass map 337 as an information map. Vegetative index map 332 includes georeferenced vegetative index values. Seeding characteristic map 333 includes georeferenced seed characteristic values. For example, seed characteristics can include the location and quantity of seeds planted. Additionally, seed characteristics can include the type of seed, genetic stalk or stem strength, genetic susceptibility to lodging, coating on the seed, genotype of the seed, etc.

Predictive yield map 335 includes georeferenced predictive yield values. Predictive yield map 335 can be generated using a process described in FIGS. 2 and 3, where the information map includes a vegetative index map or a historical yield map and the in-situ sensor includes a yield sensor. Predictive yield map 335 can be generated in other ways as well.

Predictive biomass map 337 includes georeferenced predictive biomass values. Predictive biomass map 337 can be generated using a process described in FIGS. 2 and 3, where the information map includes a vegetative index map and the in-situ sensor includes a rotor drive pressure or optical sensor, that generate sensor signals indicative of biomass. Predictive biomass map 337 can be generated in other ways as well.

Besides receiving one or more of a vegetative index map 332, seeding characteristic map 333, predictive yield map 335, or predictive biomass map 337 as an information map, predictive model generator 210 also receives a geographic location 334, or an indication of geographic location, from geographic position sensor 204. In-situ sensors 208 illustratively include an on-board crop state sensor 336 as well as a processing system 338. The processing system 338 processes sensor data generated from the on-board crop state sensors 336.

In some examples, on-board crop state sensor 336 may be an optical sensor on agricultural harvester 100. The optical sensor may be arranged at the front of agricultural harvester 100 to collect images of the field in front of agricultural harvester 100 as agricultural harvester 100 moves through the field during a harvesting operation. Processing system 338 processes one or more images obtained via the on-board crop state sensor 336 to generate processed image data identifying one or more characteristics of the crop plants in the image. For example, the magnitude and orientation of crop plant in a downed condition. Processing system 338 can also geolocate the values received from the in-situ sensor 208. For example, the location of agricultural harvester 100 at the time a signal from in-situ sensor 208 is received is typically not the accurate location of the sensed crop state. This is because it takes time from forward sensing to the time agricultural harvester 100 (equipped with the geographic position sensor) contacts the crop plants that were sensed for crop state. In some examples, to account for the forward sensing, a camera field of view can be calibrated such that areas of downed crop in an image captured by the camera can be geolocated based on their location in the image.

Other crop state sensors may also be used. In some examples, raw or processed data from on-board crop state sensor 336 may be presented to operator 260 via operator interface mechanism 218. Operator 260 may be onboard of the work agricultural harvester 100 or at a remote location.

The present discussion proceeds with respect to an example in which on-board crop state sensor 336 includes an optical sensor, such as a camera. It will be appreciated that this is just one example, and the sensors mentioned above, as other examples of on-board crop state sensor 336, are contemplated herein as well. As shown in FIG. 4, the predictive model generator 210 includes a vegetative index-to-crop state model generator 342, a yield-to-crop state model generator 344, and a biomass-to-crop state model generator 346. In other examples, the predictive model generator 210 may include additional, fewer, or different components than those shown in the example of FIG. 4. Consequently, in some examples, the predictive model generator 210 may include other items 348 as well, which may include other types of predictive model generators to generate other types of crop state models.

Model generator 342 identifies a relationship between in-situ crop state data 340 at a geographic location corresponding to where in-situ crop state data 340 were geolocated and vegetative index values from the vegetative index map 332 corresponding to the same location in the field where crop state data 340 were geolocated. Based on this relationship established by model generator 342, model generator 342 generates a predictive crop state model. The crop state model is used to predict a crop state at different locations in the field based upon the georeferenced vegetative index values contained in the vegetative index map 332 at the same locations in the field. In some examples, model generator 342 may use a time series of vegetative index maps to identify rate of crop senescence following green snap, increased crop stress from stalk damage, and other.

Model generator 344 identifies a relationship between the crop state represented in the in-situ crop state data 340, at a geographic location corresponding to where the in-situ crop state data 340 were geolocated, and the seeding characteristic value at the same location. The seeding characteristic value is the georeferenced value contained in the seeding characteristic map 333. Model generator 344 generates a predictive crop state model that predicts the crop state at a location in the field based upon the seeding characteristic value. The crop state model is used to predict a crop state at different locations in the field based upon the georeferenced seeding characteristic values contained in the seeding characteristic map 333 at the same locations in the field. The seeding characteristic, for instance, could be the seed planting density.

Model generator 345 identifies a relationship between the crop state represented in the in-situ crop state data 340, at a geographic location corresponding to where the in-situ crop state data 340 were geolocated, and the predicted yield at the same location. The predicted yield value is the georeferenced value contained in the predictive yield map 335. Model generator 345 generates a predictive crop state model that predicts the crop state at a location in the field based upon the predicted yield value. The crop state model is used to predict a crop state at different locations in the field based upon the georeferenced predictive yield values contained in the predictive yield map 335 at the same locations in the field.

Model generator 346 identifies a relationship between the crop state represented in the in-situ crop state data 340, at a geographic location corresponding to where the in-situ crop state data 340 were geolocated, and the predicted biomass at the same location. The predicted biomass value is the georeferenced value contained in the predictive biomass map 337. Model generator 346 generates a predictive crop state model that predicts the crop state at a location in the field based upon the predicted biomass value. The crop state model is used to predict a crop state at different locations in the field based upon the georeferenced predictive biomass values contained in the predictive biomass map 337 at the same locations in the field.

In light of the above, the predictive model generator 210 is operable to produce a plurality of predictive crop state models, such as one or more of the predictive crop state models generated by model generators 342, 344, 345, 346, and 348. In another example, two or more of the predictive crop state models described above may be combined into a single predictive crop state model that predicts a crop state based upon the vegetative index value, seeding characteristic value, predictive yield value, or predictive biomass values at different locations in the field. Any of these crop state models, or combinations thereof, are represented collectively by crop state model 350 in FIG. 4.

The predictive crop state model 350 is provided to predictive map generator 212. In the example of FIG. 4, predictive map generator 212 includes a crop state map generator 352. In other examples, the predictive map generator 212 may include additional, fewer, or different map generators. Crop state map generator 352 receives the predictive crop state model 350 that predicts crop state based upon a relationship between a sensed crop state value and a value from one or more of the vegetative index map 332, seeding characteristic map 333, predictive yield map 335, and predictive biomass map 337 at a corresponding location where the crop state was sensed.

Crop state map generator 354 can also generate a functional predictive crop state map 360 that predicts crop state at different locations in the field based upon the vegetative index value, seeding characteristic value, predictive yield value, or predictive biomass value at those locations in the field and the predictive crop state model 350. The generated functional predictive crop state map 360 may be provided to control zone generator 213, control system 214, or both. Control zone generator 213 generates control zones and incorporates those control zones into the functional predictive map, i.e., predictive map 360, to produce predictive control zone map 265. One or both of functional predictive maps 264 or predictive control zone map 265 may be presented to the operator 260 or anther user or be provided to control system 214, which generates control signals to control one or more of the controllable subsystems 216 based upon the predictive map 264, predictive control zone map 265, or both.

FIG. 5 is a flow diagram of an example of operation of predictive model generator 210 and predictive map generator 212 in generating the predictive crop state model 350 and the functional predictive crop state map 360. At block 362, predictive model generator 210 and predictive map generator 212 receive one or more of prior vegetative index map 332, seeding characteristic map 333, predictive yield map 335, and predictive biomass map 337.

At block 363, information map selector 209 selects one or more specific information maps 250 for use by predictive model generator 210. In some examples, information map selector 209 can change which information map is being used upon detection that one of the other candidate information maps is more closely correlating to the in-situ sensed crop state. For example, a change from vegetative index map 332 to seeding characteristic map 333 may occur where the seeding characteristic map 333 is correlating better to the crop state sensed by in-situ sensor.

At block 364, a crop state sensor signal is received from an on-board crop state sensor 336. As discussed above, the on-board crop state sensor 336 may be an optical sensor 365 or some other crop state sensor 370.

At block 372, processing system 338 processes the one or more received in-situ sensor signals received from the on-board crop state sensors 336 to generate a crop state value indicative of a crop state characteristic of the crop plants in the field proximate agricultural harvester 100.

At block 382, predictive model generator 210 also obtains the geographic location corresponding to the sensor signal. For instance, the predictive model generator 210 can obtain the geographic position from geographic position sensor 204 and determine, based upon machine delays (e.g., machine processing speed), machine speed and sensor considerations (e.g., a camera field of view, sensor calibration, etc.), a precise geographic location where the in-situ sensed crop state is to be attributed. For example, the exact time a crop state sensor signal is captured typically does not correspond to the crop state of the crop at a current geographic position of agricultural harvester 100. Instead, the current in-situ crop state sensor signal corresponds to a location on the field forward of agricultural harvester 100 since the current in-situ crop state sensor signal was sensed in an image take in front of agricultural harvester 100. This is indicated by block 378.

At block 384, predictive model generator 210 generates one or more predictive crop state models, such as crop state model 350, that model a relationship between at least one of a vegetative index value, a seeding characteristic, a predictive yield value, or a predictive biomass value obtained from an information map, such as information map 258, and a crop state being sensed by the in-situ sensor 208. For instance, predictive model generator 210 may generate a predictive crop state model based on seeding density values, which can also indicate a high crop plant population, and a sensed crop state indicated by the sensor signal obtained from in-situ sensor 208.

At block 386, the predictive crop state model, such as predictive crop state model 350, is provided to predictive map generator 212, which generates a functional predictive crop state map that maps a predicted crop state to different geographic locations in the field based on the prior vegetative index map 332, seeding characteristic map 333, predictive yield map 335, or predictive biomass map 337 and the predictive crop state model 350. For instance, in some examples, the functional predictive crop state map 360 predicts crop state. In other examples, the functional predictive crop state map 360 map predicts other items. Further, the functional predictive crop state map 360 can be generated during the course of an agricultural harvesting operation. Thus, as an agricultural harvester is moving through a field performing an agricultural harvesting operation, the functional predictive crop state map 360 is generated.

At block 394, predictive map generator 212 outputs the functional predictive crop state map 360. At block 393, predictive map generator 212 configures the functional predictive crop state map 360 for consumption by control system 214. At block 395, predictive map generator can also provide the map 360 to control zone generator 213 for generation of control zones. At block 397, predictive map generator 212 configures the map 360 in other ways as well. The functional predictive crop state map 360 (with or without the control zones) is provided to control system 214. At block 396, control system 214 generates control signals to control the controllable subsystems 216 based upon the functional predictive crop state map 360.

It can thus be seen that the present system takes an information map that maps a characteristic such as vegetative index, a seeding characteristic, a predictive yield, or a predictive biomass values to different locations in a field. The present system also uses one or more in-situ sensors that sense in-situ sensor data that is indicative of a characteristic, such as crop state, and generates a model that models a relationship between the crop state sensed in-situ using the in-situ sensor and the characteristic mapped in the information map. Thus, the present system generates a functional predictive map using a model and an information map and may configure the generated functional predictive map for consumption by a control system or for presentation to a local or remote operator or other user. For example, the control system may use the map to control one or more systems of a combine harvester.

The present discussion has mentioned processors and servers. In some examples, the processors and servers include computer processors with associated memory and timing circuitry, not separately shown. The processors and servers are functional parts of the systems or devices to which the processors and servers belong and are activated by and facilitate the functionality of the other components or items in those systems.

Also, a number of user interface displays have been discussed. The displays can take a wide variety of different forms and can have a wide variety of different user actuatable operator interface mechanisms disposed thereon. For instance, user actuatable operator interface mechanisms may include text boxes, check boxes, icons, links, drop-down menus, search boxes, etc. The user actuatable operator interface mechanisms can also be actuated in a wide variety of different ways. For instance, the user actuatable operator interface mechanisms can be actuated using operator interface mechanisms such as a point and click device, such as a track ball or mouse, hardware buttons, switches, a joystick or keyboard, thumb switches or thumb pads, etc., a virtual keyboard or other virtual actuators. In addition, where the screen on which the user actuatable operator interface mechanisms are displayed is a touch sensitive screen, the user actuatable operator interface mechanisms can be actuated using touch gestures. Also, user actuatable operator interface mechanisms can be actuated using speech commands using speech recognition functionality. Speech recognition may be implemented using a speech detection device, such as a microphone, and software that functions to recognize detected speech and execute commands based on the received speech.

A number of data stores have also been discussed. It will be noted the data stores can each be broken into multiple data stores. In some examples, one or more of the data stores may be local to the systems accessing the data stores, one or more of the data stores may all be located remote form a system utilizing the data store, or one or more data stores may be local while others are remote. All of these configurations are contemplated by the present disclosure.

Also, the figures show a number of blocks with functionality ascribed to each block. It will be noted that fewer blocks can be used to illustrate that the functionality ascribed to multiple different blocks is performed by fewer components. Also, more blocks can be used illustrating that the functionality may be distributed among more components. In different examples, some functionality may be added, and some may be removed.

It will be noted that the above discussion has described a variety of different systems, components, logic and interactions. It will be appreciated that any or all of such systems, components, logic and interactions may be implemented by hardware items, such as processors, memory, or other processing components, some of which are described below, that perform the functions associated with those systems, components, logic, or interactions. In addition, any or all of the systems, components, logic and interactions may be implemented by software that is loaded into a memory and is subsequently executed by a processor or server or other computing component, as described below. Any or all of the systems, components, logic and interactions may also be implemented by different combinations of hardware, software, firmware, etc., some examples of which are described below. These are some examples of different structures that may be used to implement any or all of the systems, components, logic and interactions described above. Other structures may be used as well.

Figure 6:
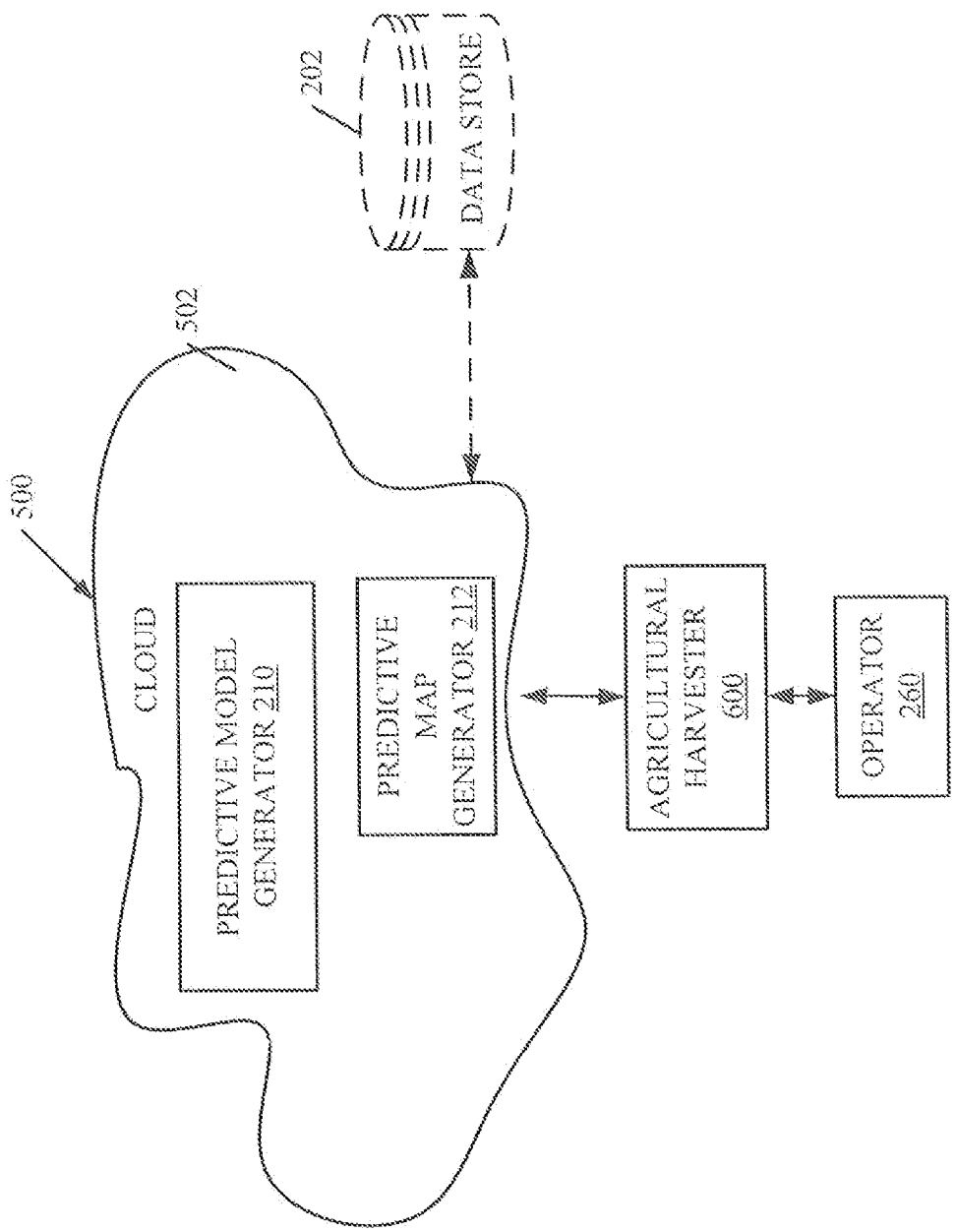
FIG. 6 is a block diagram showing one example of an agricultural harvester in communication with a remote server environment.

FIG. 6 is a block diagram of agricultural harvester 600, which may be similar to agricultural harvester 100 shown in FIG. 2. The agricultural harvester 600 communicates with elements in a remote server architecture 500. In some examples, remote server architecture 500 provides computation, software, data access, and storage services that do not require end-user knowledge of the physical location or configuration of the system that delivers the services. In various examples, remote servers may deliver the services over a wide area network, such as the internet, using appropriate protocols. For instance, remote servers may deliver applications over a wide area network and may be accessible through a web browser or any other computing component. Software or components shown in FIG. 2 as well as data associated therewith, may be stored on servers at a remote location. The computing resources in a remote server environment may be consolidated at a remote data center location, or the computing resources may be dispersed to a plurality of remote data centers. Remote server infrastructures may deliver services through shared data centers, even though the services appear as a single point of access for the user. Thus, the components and functions described herein may be provided from a remote server at a remote location using a remote server architecture. Alternatively, the components and functions may be provided from a server, or the components and functions can be installed on client devices directly, or in other ways.

In the example shown in FIG. 6, some items are similar to those shown in FIG. 2 and those items are similarly numbered. FIG. 6 specifically shows that predictive model generator 210 or predictive map generator 212, or both, may be located at a server location 502 that is remote from the agricultural harvester 600. Therefore, in the example shown in FIG. 6, agricultural harvester 600 accesses systems through remote server location 502.

FIG. 6 also depicts another example of a remote server architecture. FIG. 6 shows that some elements of FIG. 2 may be disposed at a remote server location 502 while others may be located elsewhere. By way of example, data store 202 may be disposed at a location separate from location 502 and accessed via the remote server at location 502. Regardless of where the elements are located, the elements can be accessed directly by agricultural harvester 600 through a network such as a wide area network or a local area network; the elements can be hosted at a remote site by a service; or the elements can be provided as a service or accessed by a connection service that resides in a remote location. Also, data may be stored in any location, and the stored data may be accessed by, or forwarded to, operators, users or systems. For instance, physical carriers may be used instead of, or in addition to, electromagnetic wave carriers. In some examples, where wireless telecommunication service coverage is poor or nonexistent, another machine, such as a fuel truck or other mobile machine or vehicle, may have an automated, semi-automated or manual information collection system. As the combine harvester 600 comes close to the machine containing the information collection system, such as a fuel truck prior to fueling, the information collection system collects the information from the combine harvester 600 using any type of ad-hoc wireless connection. The collected information may then be forwarded to another network when the machine containing the received information reaches a location where wireless telecommunication service coverage or other wireless coverage—is available. For instance, a fuel truck may enter an area having wireless communication coverage when traveling to a location to fuel other machines or when at a main fuel storage location. All of these architectures are contemplated herein. Further, the information may be stored on the agricultural harvester 600 until the agricultural harvester 600 enters an area having wireless communication coverage. The agricultural harvester 600, itself, may send the information to another network.

It will also be noted that the elements of FIG. 2, or portions thereof, may be disposed on a wide variety of different devices. One or more of those devices may include an on-board computer, an electronic control unit, a display unit, a server, a desktop computer, a laptop computer, a tablet computer, or other mobile device, such as a palm top computer, a cell phone, a smart phone, a multimedia player, a personal digital assistant, etc.

In some examples, remote server architecture 500 may include cybersecurity measures. Without limitation, these measures may include encryption of data on storage devices, encryption of data sent between network nodes, authentication of people or processes accessing data, as well as the use of ledgers for recording metadata, data, data transfers, data accesses, and data transformations. In some examples, the ledgers may be distributed and immutable (e.g., implemented as blockchain).

Figure 7:
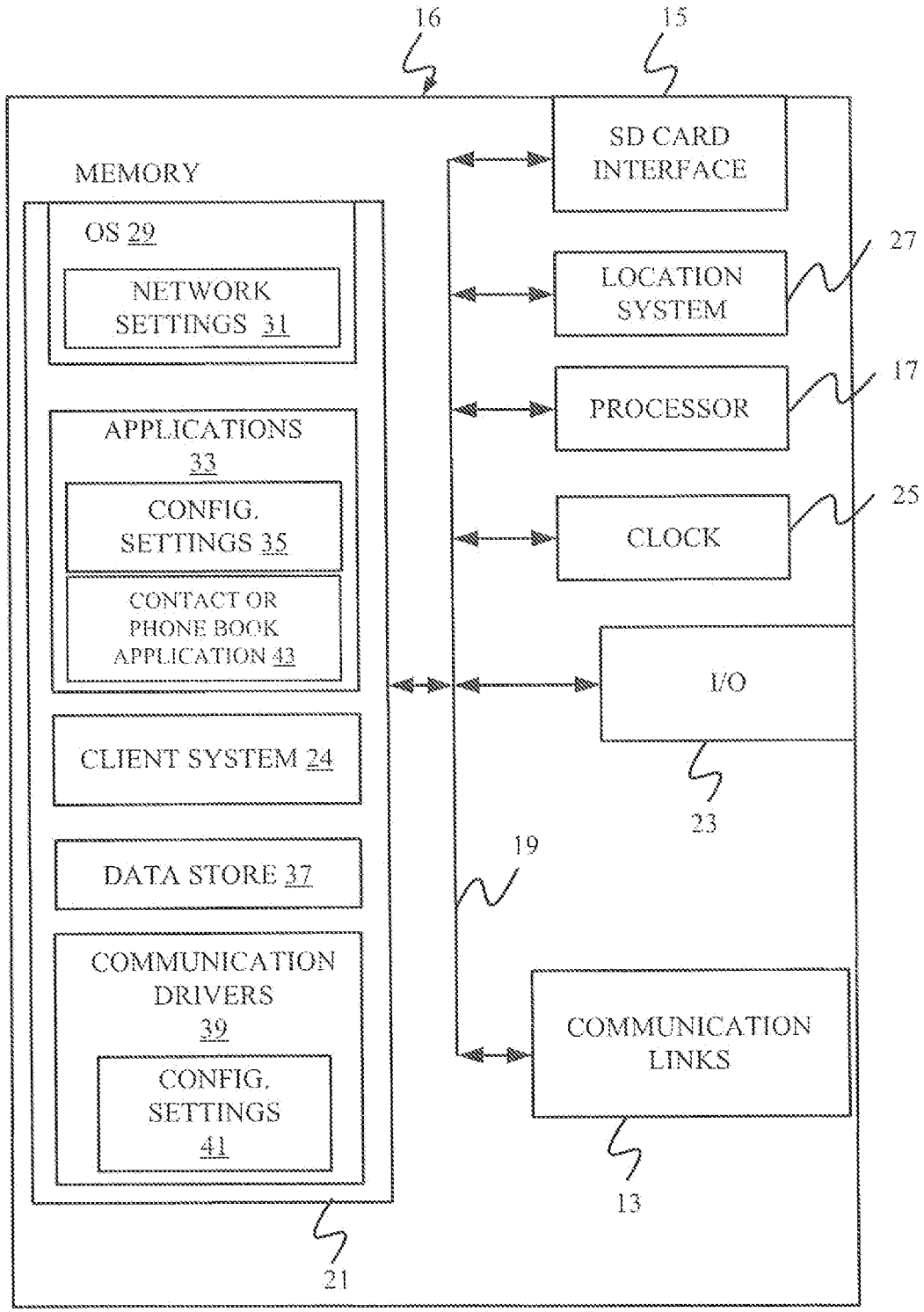
FIGS. 7-9 show examples of mobile devices that can be used in an agricultural harvester.
Figure 8:
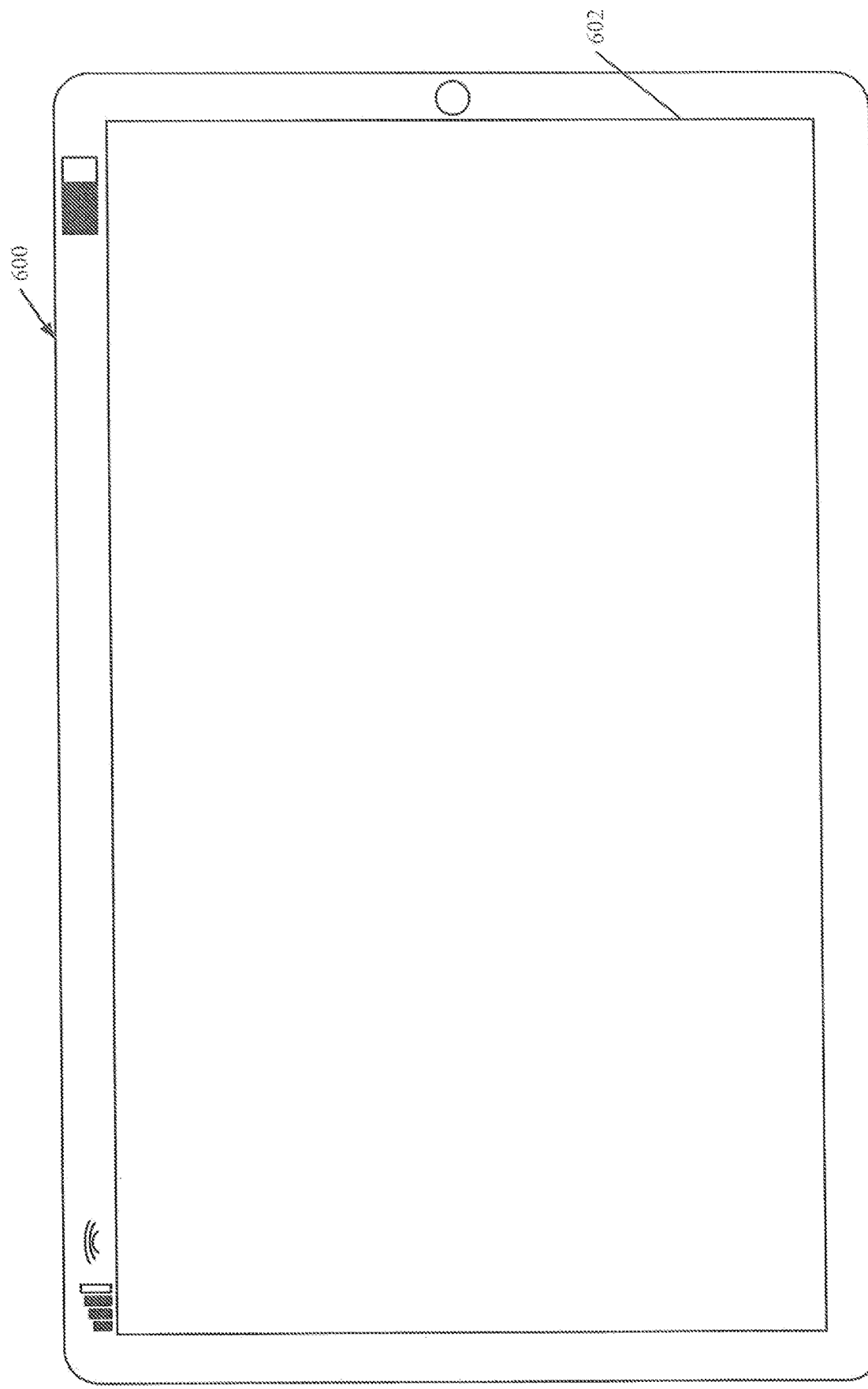
Figure 9:
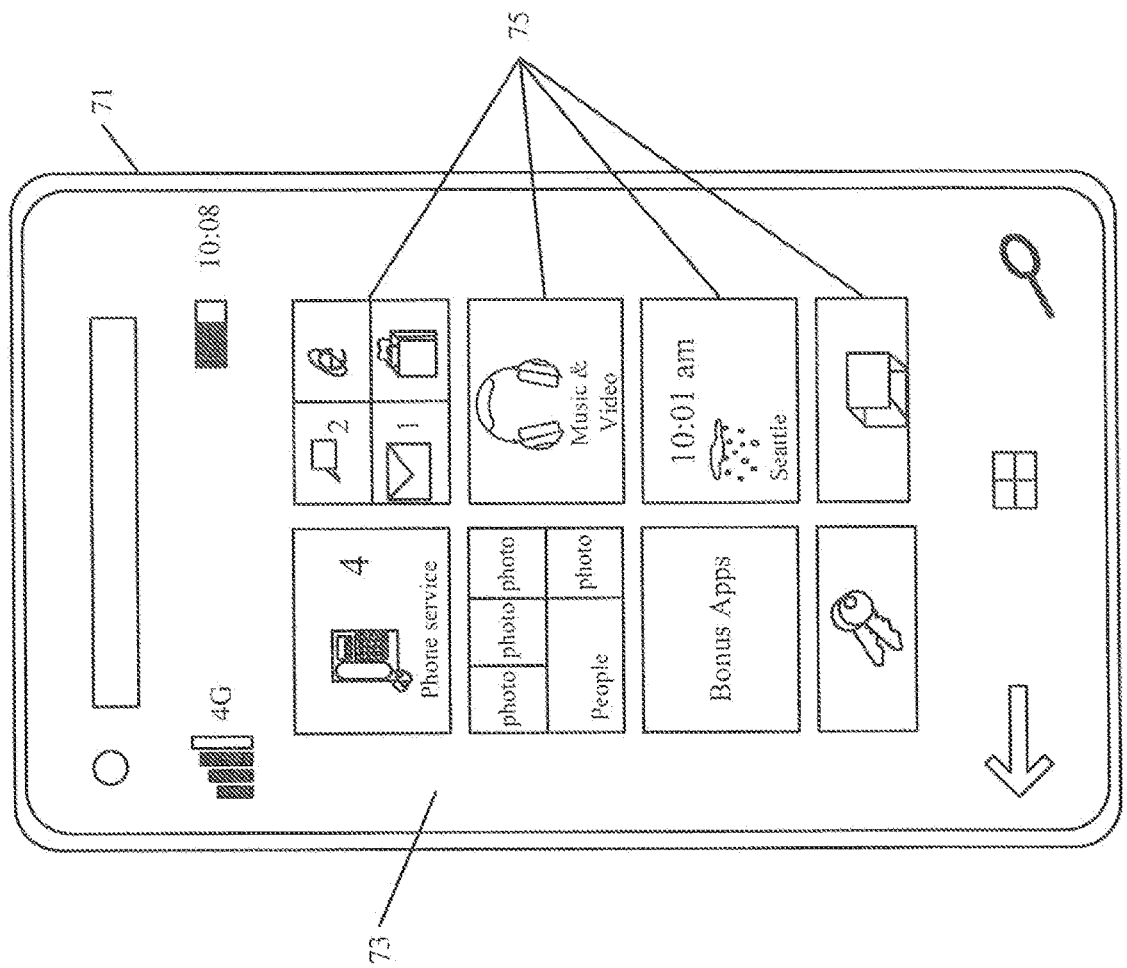

FIG. 7 is a simplified block diagram of one illustrative example of a handheld or mobile computing device that can be used as a user's or client's hand held device 16, in which the present system (or parts of it) can be deployed. For instance, a mobile device can be deployed in the operator compartment of agricultural harvester 100 for use in generating, processing, or displaying the maps discussed above. FIGS. 8-9 are examples of handheld or mobile devices.

FIG. 7 provides a general block diagram of the components of a client device 16 that can run some components shown in FIG. 2, that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from other FIGS.) along a bus that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. Location system 27 can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. Memory 21 may also include computer storage media (described below). Memory 21 stores computer readable instructions that, when executed by processor 17, cause the processor to perform computer-implemented steps or functions according to the instructions. Processor 17 may be activated by other components to facilitate their functionality as well.

FIG. 8 shows one example in which device 16 is a tablet computer 600. In FIG. 8, computer 600 is shown with user interface display screen 602. Screen 602 can be a touch screen or a pen-enabled interface that receives inputs from a pen or stylus. Tablet computer 600 may also use an on-screen virtual keyboard. Of course, computer 600 might also be attached to a keyboard or other user input device through a suitable attachment mechanism, such as a wireless link or USB port, for instance. Computer 600 may also illustratively receive voice inputs as well.

FIG. 9 is similar to FIG. 8 except that the device is a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 10:
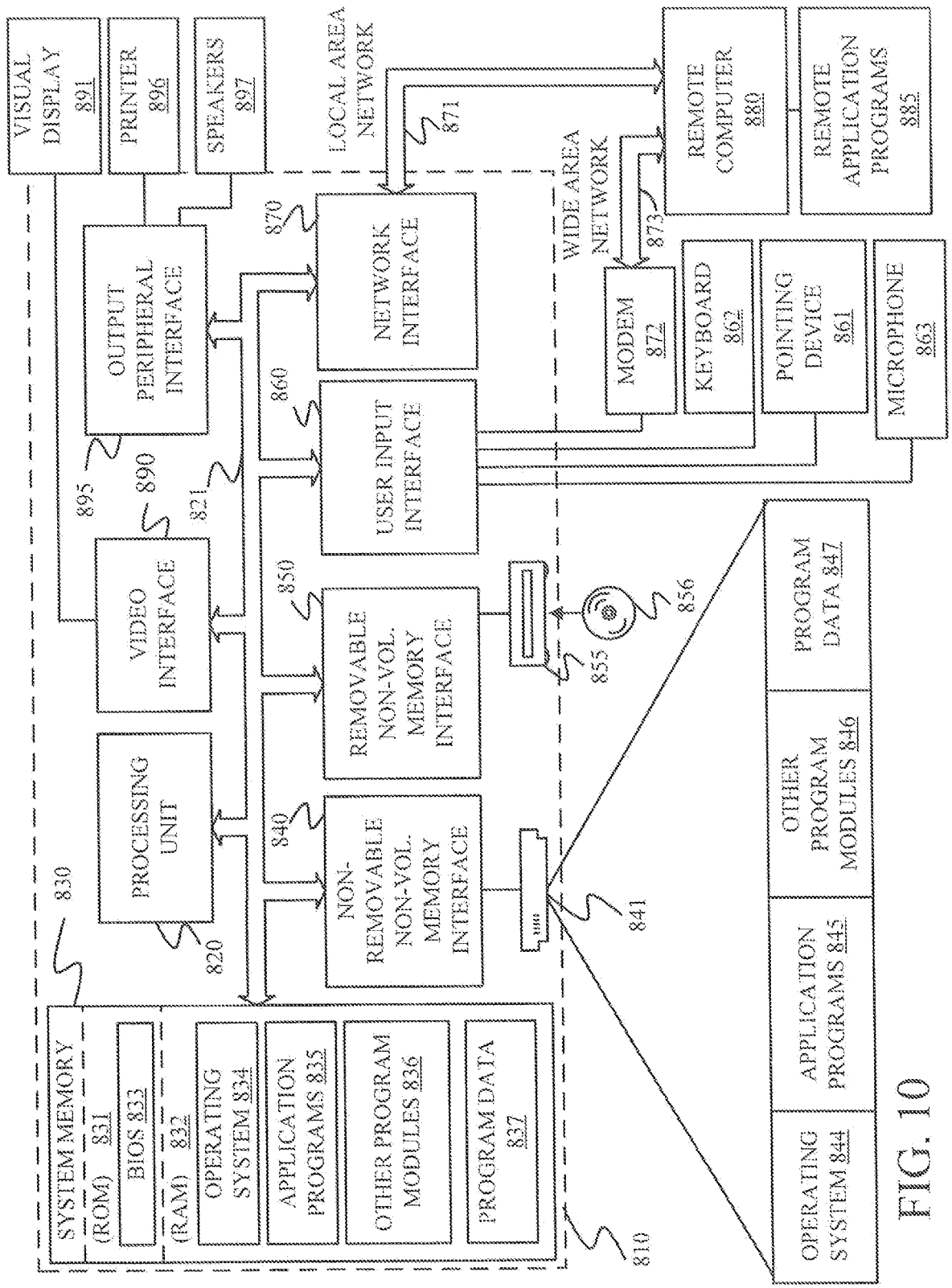
FIG. 10 is a block diagram showing one example of a computing environment that can be used in an agricultural harvester and the architectures illustrated in previous figures.

FIG. 10 is one example of a computing environment in which elements of FIG. 2 can be deployed. With reference to FIG. 10, an example system for implementing some embodiments includes a computing device in the form of a computer 810 programmed to operate as discussed above. Components of computer 810 may include, but are not limited to, a processing unit 820 (which can comprise processors or servers from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 2 can be deployed in corresponding portions of FIG. 10.

Computer 810 typically includes a variety of computer readable media. Computer readable media may be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. Computer readable media includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory or both such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data or program modules or both that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a controller area network—CAN, local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural work machine comprising:
a communication system that receives an information map that includes values of a first agricultural characteristic corresponding to different geographic locations in a field;
a geographic position sensor that detects a geographic location of the agricultural work machine;
an in-situ sensor that detects a crop state as a second agricultural characteristic corresponding to the geographic location;
a predictive model generator that generates a predictive agricultural model that models a relationship between the first agricultural characteristic and the second agricultural characteristic based on a value of the first agricultural characteristic in the information map at the geographic location and a value of the second agricultural characteristic sensed by the in-situ sensor at the geographic location; and
a predictive map generator that generates a functional predictive agricultural map of the field that maps predictive values of the second agricultural characteristic to the different geographic locations in the field based on the values of the first agricultural characteristic in the information map and based on the predictive agricultural model.

Example 2 is the agricultural work machine of any or all previous examples, wherein the predictive map generator configures the functional predictive agricultural map for consumption by a control system that generates control signals to control a controllable subsystem on the agricultural work machine based on the functional predictive agricultural map.

Example 3 is the agricultural work machine of any or all previous examples, wherein the in-situ sensor generates sensor data indicative of the crop state and wherein the in-situ sensor comprises:
a processing system configured to analyze the sensor data and determine at least one of an orientation or a magnitude of the crop state.

Example 4 is the agricultural work machine of any or all previous examples, wherein the information map comprises a prior vegetative index map that maps, as the first agricultural characteristic, vegetative index values to the different geographic locations in the field.

Example 5 is the agricultural work machine of any or all previous examples, wherein the predictive model generator is configured to identify the relationship between the crop state detected at the geographic location and a vegetative index value of the vegetative index values in the prior vegetative index map at the geographic location, the predictive agricultural model being configured to receive an input vegetative index value as a model input and generate a predicted crop state value as a model output based on the identified relationship.

Example 6 is the agricultural work machine of any or all previous examples, wherein the information map comprises a seeding characteristic map that maps, as the first agricultural characteristic, seeding characteristic values to the different geographic locations in the field.

Example 7 is the agricultural work machine of any or all previous examples, wherein the predictive model generator is configured to identify the relationship between the crop state detected at the geographic location and a seeding characteristic in the seeding characteristic map at the geographic location, the predictive agricultural model being configured to receive an input seeding characteristic value as a model input and generate a predicted crop state value as a model output based on the identified relationship.

Example 8 is the agricultural work machine of any or all previous examples, wherein the seeding characteristic comprises genetic stalk or stem strength.

Example 9 is the agricultural work machine of any or all previous examples, wherein the seeding characteristic comprises genetic susceptibility to lodging.

Example 10 is the agricultural work machine of any or all previous examples, wherein the information map comprises a predictive map that maps, as the first agricultural characteristic, predictive yield or predictive biomass values to the different geographic locations in the field.

Example 11 is the agricultural work machine of any or all previous examples, wherein the predictive model generator is configured to identify the relationship between the crop state detected at the geographic location and the predictive yield or the predictive biomass in the predictive map at the geographic location, the predictive agricultural model being configured to receive an input yield or biomass value as a model input and generate a predicted crop state value as a model output based on the identified relationship.

Example 12 is a computer implemented method of generating a functional predictive agricultural map, the computer implemented method comprising:
receiving an information map at an agricultural work machine that indicates values of a first agricultural characteristic corresponding to different geographic locations in a field;
detecting a geographic location of the agricultural work machine;
detecting, with an in-situ sensor, a crop state as a second agricultural characteristic corresponding to the geographic location;
generating a predictive agricultural model that models a relationship between the first agricultural characteristic and the second agricultural characteristic; and
controlling a predictive map generator to generate the functional predictive agricultural map of the field that maps predictive values of the second agricultural characteristic to the different locations in the field based on the values of the first agricultural characteristic in the information map and the predictive agricultural model.

Example 13 is the computer implemented method of any or all previous examples, and further comprising:
configuring the functional predictive agricultural map for a control system that generates control signals to control a controllable subsystem on the agricultural work machine based on the functional predictive agricultural map.

Example 14 is the computer implemented method of any or all previous examples, wherein receiving the information map comprises receiving a prior vegetative index map that maps, as the first agricultural characteristic, vegetative index values to the different geographic locations in the field.

Example 15 is the computer implemented method of any or all previous examples, wherein generating the predictive agricultural model comprises:
identifying the relationship between the vegetative index values and the crop state based on the crop state detected at the geographic location and a vegetative index value of the vegetative index values in the prior vegetative index map at the geographic location; and
controlling a predictive model generator to generate the predictive agricultural model that receives an input vegetative index value as a model input and generates a predicted crop state value as a model output based on the identified relationship.

Example 16 is the computer implemented method of any or all previous examples, wherein receiving the information map comprises receiving a seeding characteristic map that maps, as the first agricultural characteristic, seeding characteristic values to the different geographic locations in the field.

Example 17 is the computer implemented method of any or all previous examples, wherein generating the predictive agricultural model comprises:
identifying the relationship between the seeding characteristic values and the crop state based on the crop state detected at the geographic location and the seeding characteristic values in the seeding characteristic map at the geographic location; and
controlling a predictive model generator to generate the predictive agricultural model that receives an input seeding characteristic value as a model input and generates a predicted crop state value as a model output based on the identified relationship.

Example 18 is the computer implemented method of any or all previous examples, wherein the seeding characteristic values comprise seed planting density values.

Example 19 is an agricultural work machine comprising:
a communication system that receives a prior vegetative index map that indicates vegetative index values corresponding to different geographic locations in a field;
a geographic position sensor that detects a geographic location of the agricultural work machine;
an in-situ sensor that detects a crop state characteristic corresponding to the geographic location;
a predictive model generator that generates a predictive crop state model that models a relationship between the first characteristic values and the crop state characteristic based on a vegetative index value in the prior vegetative index map at the geographic location and the crop state characteristic sensed by the in-situ sensor at the geographic location; and
a predictive map generator that generates a functional predictive crop state map of the field that maps predictive crop state values to the different locations in the field based on the vegetative index values in the prior vegetative index map and based on the predictive crop state model.

Example 20 is the agricultural work machine of any or all previous examples, wherein the in-situ sensor comprises an optical sensor and wherein the geographic position sensor detects the geographic location a given time after the in-situ sensor detects the crop state characteristic corresponding to the geographic location, a length of the given time being based at least in part on a machine speed and a field of view of the optical sensor.

Although the subject matter has been described in language specific to structural features or methodological acts, it is to be understood that the subject matter defined in the appended claims is not necessarily limited to the specific features or acts described above. Rather, the specific features and acts described above are disclosed as example forms of the claims

What is claimed is:
1. An agricultural work machine comprising:
a communication system configured to obtain an information map that includes values of a first agricultural characteristic corresponding to different geographic locations in a field;
a geographic position sensor configured to detect a geographic location of the agricultural work machine;

an in-situ sensor configured to detect, as a value of a second agricultural characteristic, a crop state value corresponding to the geographic location; and a predictive model generator configured to generate a predictive agricultural model that models a relationship between the first agricultural characteristic and the second agricultural characteristic based on a value of the first agricultural characteristic in the information map corresponding to the geographic location and the detected value of the second agricultural characteristic corresponding to the geographic location.

2. The agricultural work machine of claim 1, a control system configured to generate a control signal to control a controllable subsystem on the agricultural work machine based on the predictive agricultural model.

3. The agricultural work machine of claim 1, wherein the crop state value indicates at least one of a magnitude or a direction of leaning of a crop to which the crop state value corresponds.

4. The agricultural work machine of claim 1, wherein the information map comprises a vegetative index map that includes, as the values of the first agricultural characteristic, vegetative index values corresponding to the different geographic locations in the field, and wherein the predictive model generator is configured to model, as the relationship, a relationship between crop state and vegetative index based on the detected crop state value corresponding to the geographic location and a vegetative index value in the vegetative index map corresponding to the geographic location, the predictive agricultural model being configured to receive an input vegetative index value as a model input and generate a predictive crop state value as a model output based on the modeled relationship.

5. The agricultural work machine of claim 1, wherein the information map comprises a seeding characteristic map that includes, as values of the first agricultural characteristic, values of a seeding characteristic corresponding to the different geographic locations in the field and wherein the predictive agricultural model models, as the relationship, a relationship between crop state and the seeding characteristic based on the detected crop state value corresponding to the geographic location and a value of the seeding characteristic in the seeding characteristic map corresponding to the geographic location, the predictive agricultural model being configured to receive an input value of the seeding characteristic as a model input and generate a predictive crop state value as a model output based on the modeled relationship.

6. The agricultural work machine of claim 5, wherein the seeding characteristic comprises one of:
genetic stalk or stem strength;
genetic susceptibility to lodging; or
seed planting density.

7. The agricultural work machine of claim 1, wherein the information map is based on sensor readings of one or more bands of electromagnetic radiation.

8. The agricultural work machine of claim 1, wherein the information map comprises a yield map that includes, as the values of the first agricultural characteristic, yield values corresponding to the different geographic locations in the field and wherein the predictive agricultural model models, as the relationship, a relationship between crop state and yield based on the detected crop state value corresponding to the geographic location and a yield value in the yield map corresponding to the geographic location, the predictive agricultural model being configured to receive an input yield value as a model input and generate a predictive crop state value as a model output based on the modeled relationship.

9. The agricultural work machine of claim 1, wherein the information map comprises a biomass map that includes, as the values of the first agricultural characteristic, biomass values corresponding to the different geographic locations in the field and wherein the predictive agricultural model models, as the relationship, a relationship between crop state and biomass based on the detected crop state value corresponding to the geographic location and a biomass value in the yield map corresponding to the geographic location, the predictive agricultural model being configured to receive an input biomass value as a model input and generate a predictive crop state value as a model output based on the modeled relationship.

10. The agricultural work machine of claim 1 and further comprising:
a predictive map generator that generates a functional predictive agricultural map of the field that maps predictive values of the second agricultural characteristic to the different geographic locations in the field based on the values of the first agricultural characteristic in the information map and based on the predictive agricultural model.

11. The agricultural work machine of claim 10 and further comprising:
a control system configured to generate a control signal to control a controllable subsystem on the agricultural work machine based on the functional predictive agricultural map.

12. A computer implemented method of generating a predictive agricultural model, the computer implemented method comprising:
obtaining an information map that includes values of a first agricultural characteristic corresponding to different geographic locations in a field,
detecting a geographic location of an agricultural work machine;
detecting, with an in-situ sensor, as a value of a second agricultural characteristic, a crop state value corresponding to the geographic location; and
generating a predictive agricultural model that models a relationship between the first agricultural characteristic and the second agricultural characteristic based on a value of the first agricultural characteristic in the information map corresponding to the geographic location and the detected value of the second agricultural characteristic corresponding to the geographic location.

13. The computer implemented method of claim 12, and further comprising:
generating a control signal to control a controllable subsystem on the agricultural work machine based on the predictive agricultural model.

14. The computer implemented method of claim 12, wherein obtaining the information map comprises obtaining, as the information map, a vegetative index map that includes, as the values of the first agricultural characteristic, vegetative index values corresponding to the different geographic locations in the field and wherein generating the predictive agricultural model comprises:
generating the predictive model modeling, as the relationship, a relationship between vegetative index and crop state based on the detected value of crop state corresponding to the geographic location and a vegetative index value in the vegetative index map corresponding to the geographic location; and controlling a predictive model generator to generate the predictive agricultural model as being configured to receive an input vegetative index value as a model input and to generate a predictive crop state value as a model output based on the modeled relationship.

15. The computer implemented method of claim 12, wherein obtaining the information map comprises obtaining, as the information map, a seeding characteristic map that includes, as the values of first agricultural characteristic, values of a seeding characteristic corresponding to the different geographic locations in the field and wherein generating the predictive agricultural model comprises:

generating the predictive model modeling, as the relationship, a relationship between crop state and the seeding characteristic based on the detected value of crop state corresponding to the geographic location and a value of the seeding characteristic in the seeding characteristic map corresponding to the geographic location; and controlling a predictive model generator to generate the predictive agricultural model as being configured to receives an input value of the seeding characteristic as a model input and generate a predictive crop state value as a model output based on the modeled relationship.

16. The computer implemented method of claim 12, wherein obtaining the information map comprises obtaining, as the information map, an information map that includes values of the first agricultural characteristic corresponding to the different geographic locations in the field and is derived from sensor readings of visible light.

17. The computer implemented method of claim 12 and further comprising:

generating a functional predictive agricultural map of the field that maps predictive values of the second agricultural characteristic to the different locations in the field based on values of the first agricultural characteristic in the information map and the predictive agricultural model; and generating a control signal to control a controllable subsystem on the agricultural work machine based on the functional predictive agricultural map.

18. An agricultural-work system comprising:

a communication system configured to obtain an information map that includes values of a first agricultural characteristic corresponding to different geographic locations in a field;

a geographic position sensor configured to detect a geographic location of the agricultural work machine;

an in-situ sensor configured to detect, as a value of a second agricultural characteristic, a crop state value corresponding to the geographic location; and a predictive model generator configured to generate a predictive agricultural model that models a relationship between the first agricultural characteristic and the second agricultural characteristic based on a value of the first agricultural characteristic in the information map corresponding to the geographic location and the detected value of the second agricultural characteristic corresponding to the geographic location.

19. The agricultural system of claim 18 and further comprising:

a predictive map generator that generates a functional predictive agricultural map of the field that maps predictive values of the second agricultural characteristic to the different geographic locations in the field based on the values of the first agricultural characteristic in the information map and based on the predictive agricultural model; and a control system that generates a control signal to control a controllable subsystem on the agricultural work machine based on the functional predictive agricultural map.

20. The agricultural system of claim 18, wherein the information map is based on sensor readings of visible light reflected from crop plants at the worksite.

\* \* \* \* \*